United States Patent
Oshlack et al.

(10) Patent No.: US 7,070,806 B2
(45) Date of Patent: *Jul. 4, 2006

(54) CONTROLLED RELEASE FORMULATIONS COATED WITH AQUEOUS DISPERSIONS OF ACRYLIC POLYMERS

(75) Inventors: Benjamin Oshlack, New York, NY (US); Mark Chasin, Manalapan, NJ (US); Frank Pedi, Jr., Yorktown Heights, NY (US)

(73) Assignee: Purdue Pharma LP, Stamford, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/273,434

(22) Filed: Oct. 17, 2002

(65) Prior Publication Data

US 2003/0198673 A1 Oct. 23, 2003

Related U.S. Application Data

(60) Continuation of application No. 09/707,276, filed on Nov. 6, 2000, now abandoned, which is a continuation of application No. 08/816,023, filed on Mar. 11, 1997, now Pat. No. 6,143,353, which is a division of application No. 08/459,110, filed on Jun. 2, 1995, now Pat. No. 5,639,476, which is a division of application No. 08/097,558, filed on Jul. 27, 1993, now Pat. No. 5,580,578, which is a continuation-in-part of application No. 07/826,084, filed on Jan. 27, 1992, now Pat. No. 5,286,493.

(51) Int. Cl.
*A61K 9/22* (2006.01)
*A61K 9/32* (2006.01)
*A61K 9/50* (2006.01)
*A61K 9/28* (2006.01)
*A01N 25/26* (2006.01)

(52) U.S. Cl. .................. 424/468; 424/482; 424/417; 427/2.21; 427/2.14; 427/221

(58) Field of Classification Search .............. 427/2.21, 427/221, 2.14; 424/490, 458, 461, 462, 480, 424/482, 495, 497, 468, 417
See application file for complete search history.

(56) References Cited

U.S. PATENT DOCUMENTS 3,901,968 A 8/1975 Cohen et al. ................. 424/22

(Continued)

FOREIGN PATENT DOCUMENTS

AU 653223 11/1992

(Continued)

OTHER PUBLICATIONS

D.L. Munday, A.R. Fassihi, 5$^{th}$ Congr. Int. Tech. Pharm. vol. 2, pp 55-60 Changes in Drug Release Rate, Effect of Temperature and Relative Humidity on Polymeric Film Coating, 1989, Assoc. Pharm. Galenique Ind., Chatenay Malabry, FR.

(Continued)

*Primary Examiner*—Shengjun Wang
(74) *Attorney, Agent, or Firm*—Davidson Davidson and Kappel, LLC

(57) ABSTRACT

A stable solid controlled release formulation having a coating derived from an aqueous dispersion of a hydrophobic acrylic polymer includes a substrate including an active agent selected from the group consisting of a systemically active therapeutic agent, a locally active therapeutic agent, a disinfecting and sanitizing agent, a cleansing agent, a fragrance agent and a fertilizing agent, overcoated with an aqueous dispersion of the plasticized water-insoluble acrylic polymer. The formulation provides a stable dissolution of the active agent which is unchanged after exposure to accelerated storage conditions.

39 Claims, 7 Drawing Sheets

U.S. PATENT DOCUMENTS

| | | | |
|---|---|---|---|
| 3,901,969 A | 8/1975 | Cohen et al. | 424/22 |
| 3,935,326 A | 1/1976 | Groppenbacher et al. | 427/3 |
| 4,017,647 A | 4/1977 | Ohno et al. | 424/2.16 |
| 4,026,932 A | 5/1977 | Gross et al. | 260/29.6 H |
| 4,060,598 A | 11/1977 | Groppenbacher et al. | 424/33 |
| 4,088,798 A | 5/1978 | Michaelis | 427/3 |
| 4,359,483 A | 11/1982 | Kaetsu et al. | 424/2.21 |
| 4,443,497 A | 4/1984 | Samelima et al. | 427/213.36 |
| 4,520,172 A | 5/1985 | Lehmann et al. | 525/369 |
| 4,548,990 A | 10/1985 | Mueller et al. | 525/123 |
| 4,553,973 A | 11/1985 | Edgren | 427/2.16 |
| 4,600,645 A | 7/1986 | Ghebre-Sellassie et al. | 428/403 |
| 4,705,695 A | 11/1987 | Lehmann et al. | 427/3 |
| 4,716,041 A | 12/1987 | Kjornaes et al. | 424/468 |
| 4,728,513 A | 3/1988 | Ventouras | 424/461 |
| 4,766,012 A | 8/1988 | Valenti | 427/213.36 |
| 4,784,858 A | 11/1988 | Ventouras | 424/468 |
| 4,786,505 A | 11/1988 | Lovgren et al. | 424/466 |
| 4,786,506 A | 11/1988 | Fontanelli | 424/470 |
| 4,798,724 A | 1/1989 | Khanna | 424/33 |
| 4,837,004 A | 6/1989 | Wu et al. | 424/438 |
| 4,853,230 A | 8/1989 | Lovgren et al. | 424/466 |
| 4,891,230 A | 1/1990 | Geogheogan et al. | 424/461 |
| 4,954,350 A | 9/1990 | Jones et al. | 424/493 |
| 5,008,118 A | 4/1991 | Iwanami et al. | 424/498 |
| 5,019,397 A | 5/1991 | Wong et al. | 424/470 |
| 5,024,842 A | 6/1991 | Edgren et al. | 424/473 |
| 5,047,258 A | 9/1991 | Belanger et al. | 427/3 |
| 5,068,110 A | 11/1991 | Fawzi et al. | 424/462 |
| 5,084,278 A | 1/1992 | Mehta | 424/441 |
| 5,085,866 A | 2/1992 | Cowsar et al. | |
| 5,091,175 A | 2/1992 | Imondi et al. | 424/486 |
| 5,096,717 A | 3/1992 | Wirth et al. | 424/490 |
| 5,112,384 A | 5/1992 | Miura et al. | |
| 5,112,621 A | 5/1992 | Stevens et al. | 424/497 |
| 5,122,384 A | 6/1992 | Paradissis et al. | 424/451 |
| 5,130,171 A | 7/1992 | Prud'Homme et al. | 427/213.36 |
| 5,133,974 A | 7/1992 | Paradissis et al. | 424/480 |
| 5,158,777 A | 10/1992 | Abramowitz et al. | 424/458 |
| 5,160,742 A | 11/1992 | Hazer et al. | 424/470 |
| 5,160,743 A | 11/1992 | Edgren et al. | 424/473 |
| 5,171,580 A | 12/1992 | Iamartino et al. | 424/490 |
| 5,178,866 A | 1/1993 | Wright et al. | 424/473 |
| 5,189,148 A | 2/1993 | Akiyama et al. | 530/399 |
| 5,202,128 A | 4/1993 | Morella et al. | 424/469 |
| 5,202,159 A | 4/1993 | Chen et al. | 427/213.31 |
| 5,219,621 A | 6/1993 | Geoghegan et al. | 424/462 |
| 5,286,493 A * | 2/1994 | Oshlack et al. | 424/468 |
| 5,288,505 A | 2/1994 | Deboeck et al. | 424/497 |
| 5,294,448 A | 3/1994 | Ring et al. | 424/497 |
| 5,324,523 A | 6/1994 | Zsuga et al. | 424/486 |
| 5,346,542 A | 9/1994 | Yosuke et al. | 106/194 |
| 5,395,628 A | 3/1995 | Noda et al. | 424/490 |
| 5,445,829 A | 8/1995 | Paradissis et al. | 427/2.21 |
| 5,472,712 A | 12/1995 | Oshlack et al. | 427/2.16 |
| 5,505,983 A | 4/1996 | Kamada et al. | 427/2.21 |
| 5,560,930 A | 10/1996 | Maruyama et al. | 424/488 |
| 5,580,578 A | 12/1996 | Oshlack et al. | 424/468 |
| 5,614,220 A | 3/1997 | Hirakawa et al. | 424/480 |
| 5,639,476 A | 6/1997 | Oshlack et al. | 424/468 |
| 5,681,581 A | 10/1997 | Dunn | 424/468 |
| 5,958,459 A | 9/1999 | Chasin et al. | 424/490 |
| 6,143,322 A | 11/2000 | Sackler et al. | 424/459 |
| 6,143,353 A * | 11/2000 | Oshlack et al. | 427/2.21 |

FOREIGN PATENT DOCUMENTS

| | | | |
|---|---|---|---|
| EP | 0327295 | 1/1989 | |
| EP | 0377517 | 1/1990 | |
| EP | 377517 | 1/1990 | |
| EP | 377518 | 1/1990 | |
| EP | 0377518 | 1/1990 | |
| EP | 0463877 | 6/1991 | |
| EP | 463 877 | 1/1992 | |
| EP | 0463877 | 1/1992 | |
| EP | 0514814 | 11/1992 | |
| EP | 0 553 392 | 8/1993 | |
| EP | 0553392 | 8/1993 | |
| EP | 0 631 781 | 1/1995 | |
| EP | 0631781 | 1/1995 | |
| GB | 2 178 313 | 2/1987 | |
| GB | 2178313 | 2/1987 | |
| JP | 60166608 | 8/1985 | |
| JP | 0166608 | 8/1995 | 424/472 |
| WO | WO 93/09785 | 5/1993 | |
| WO | WO9309785 | 5/1993 | |

OTHER PUBLICATIONS

D.L. Munday, A.R. Fassihi, 5h Congr. Int. Tech. Pharm. vol. 2, pp 55-60 Changes in Drug Release Rate, Effect of Temperature and Relative Humidity on Polymeric Film Coating, 1989, Assoc. Pharm. Galenique Ind., Chatenay Malabry, FR.

K. Lehman, Aqueous Coatings on Solid Pharmaceutical Dosage Forms, Rohm GmbH, Maritim Hotel Konigswinter, Rheinallee 3, D-5330 Konigswinter, Course 549 from Sep. 30th to Oct. 2nd 1991, (with translation and list of attendees).

K. Lehman, et al., Practical Work Experience of Film Coating, 1989, Rohm Pharma GmbH (with translation).

S.Li, et al., Drug Development and Industrial Pharmacy, Preparation and in-vitro Exaluation of a Controlled Release Drug Delivery System of Theophylline Unsing an Aqueous Acrylic Resin Dispersion, 15(8), pp. 1231-1241 (1989).

Polymer Handbook, pp. 209-227 (1989).

C.Lorck, Aqueous Coatings on Solid Pharmaceutical Dosage Forms, Klinge Pharma GmbH, Maritim Hotel Konigswinter, Rheinallee 3, D-5330 Konigswinter, Course 549 from Sep. 30th to 2nd Oct. 1991, (with translation).

J. Cowie, Chemistry and Physics of Polymers, An Introduction, Verlag Chemie Weinheim, N.Y. 1976, pp. 209-213.

* cited by examiner

CONTROLLED RELEASE FORMULATIONS COATED WITH AQUEOUS DISPERSIONS OF ACRYLIC POLYMERS

This application is a continuation application of Ser. No. 09/707,276, filed Nov. 6, 2000 now abandoned, which is a continuation application of Ser. No. 08/816,023, filed Mar. 11, 1997, now U.S. Pat. No. 6,143,353, which is a divisional of Ser. No. 08/459,110, filed Jun. 2, 1995, now U.S. Pat. No. 5,639,476, which is a divisional of Ser. No. 08/097,558, filed Jul. 27, 1993, now U.S. Pat. No. 5,580,578, which is a continuation-in-part of Ser. No. 07/826,084, filed Jan. 27, 1992, now U.S. Pat. No. 5,286,493.

BACKGROUND OF THE INVENTION

An important aspect of the manufacture, regulatory review and approval of all dosage forms concerns their stability over extended periods of time. The stability data obtained with regard to a particular dosage form directly affects its shelf-life. The stability of a pharmaceutical dosage form is related to maintaining its physical, chemical, microbiological, therapeutic, and toxicological properties when stored, i.e., in a particular container and environment. Stability study requirements are covered, e.g., in the Good Manufacturing Practices (GMPs), the U.S.P., as well as in the regulatory requirements of the country where approval to market a dosage form is being sought. In the United States, a request to test, and eventually market, a drug or a drug formulation may be made via a New Drug Application (NDA), an Abbreviated New Drug Application (ANDA) or an Investigational New Drug Applications (IND).

The agents used in sustained release dosage formulations often present special problems with regard to their physical stability during storage. For example, waxes which have been used in such formulations are known to undergo physical alterations on prolonged standing, thus precautions are taken to stabilize them at the time of manufacture or to prevent the change from occurring. Fats and waxy materials when used in purified states are known to crystallize in unstable forms, causing unpredictable variations in availability rates during stability testing at the time of manufacture and during later storage.

It is known that certain strategies can be undertaken to obtain stabilized controlled release formulations in many cases, such as insuring that the individual agents are in a stable form before they are incorporated into the product, and that processing does not change this condition, retarding the instability by including additional additives, and inducing the individual agents of the dosage form to reach a stable state before the product is finally completed.

It is also recognized that the moisture content of the product can also influence the stability of the product. Changes in the hydration level of a polymeric film, such as the ethyl celluloses, can alter the rate of water permeation and drug availability. Also, binders such as acacia are known to become less soluble when exposed to moisture and heat. However, moisture content of a product can be controlled fairly successfully by controls in the processing method and proper packaging of the product.

Hydrophobic polymers such as certain cellulose derivatives, zein, acrylic resins, waxes, higher aliphatic alcohols, and polylactic and polyglycolic acids have been used in the prior art to develop controlled release dosage forms. Methods of using these polymers to develop controlled release dosage forms such as tablets, capsules, suppositories, spheroids, beads or microspheres include incorporating these agents into a controlled release matrix or using certain of these agents in a controlled release coating of the dosage form. It is known in the prior art that hydrophobic coatings can be applied either from a solution, suspension or dry. Since most of the polymers used in controlled release coatings have a low solubility in water, they are usually applied by dissolving the polymer in an organic solvent and spraying the solution onto the individual drug forms (such as beads or tablets) and evaporating off the solvent.

Aqueous dispersions of hydrophobic polymers have been used in the prior art to coat pharmaceutical dosage forms for aesthetic reasons such as film coating tablets or beads or for taste-masking. However, these dosage forms are used for immediate release administration of the active drug contained in the dosage form.

The use of organic solvents in the preparation of hydrophobic coatings is considered undesirable because of inherent problems with regard to flammability, carcinogenicity, environmental concerns, cost, and safety in general. It is considered very desirable in the art, however, to provide a controlled release coating derived from aqueous dispersions of a hydrophobic material, such as an acrylic polymer.

While many formulations have been experimentally prepared which rely upon a hydrophobic coating derived from an aqueous dispersion to provide controlled release of an active agent, such formulations have not proven to be commercially viable because of stability problems. Aqueous polymeric dispersions have been used to produce stable controlled release dosage forms, but this has only been possible by other methods such as incorporation of the same into the matrix of the dosage form, rather than via the use of a coating of the aqueous polymeric dispersion to obtain retardant properties.

When coating using aqueous polymeric dispersions to obtain a desired release profile of the active agent(s) over several hours or longer, it is known in the art that the dissolution release profile changes on ageing, e.g. when the final coated product is stored for a period of time, during which time it may be exposed to elevated temperature and/or humidity above ambient conditions.

This was recently demonstrated by Munday, et al., Drug Devel. and Indus. Phar., 17 (15) 2135–2143 (1991), which reported the effect of storing theophylline mini-tablets film coated with ethyl cellulose with PEG (2:1 ratio; total coating=3% w/w), ethyl cellulose with Eudragit® L (2:1 ratio; total coating=3% w/w); and Eudragit® RL (amount of coating=1.5% w/w) at varying temperatures and relative humidities upon the rate of drug release. Samples were subjected to isothermal storage at 28° C., 35° C. and 45° C. with the relative humidity (RH) maintained between 55–60%, under cyclic conditions of 45° C. at 55% RH for 24 hours, then at 28° C. and 20% RH for 24 hours, and then at 5° C. and 10% RH for 24 hours, after which the cycle was repeated, and alternating conditions every 24 hours between 45° C. and 55% RH and 28° C. and 0% RH. The aging process brought about by storage under the above stress conditions impeded dissolution, irrespective of the nature of the polymeric film. The greatest reduction in release rate was said to occur in the first 21 days (isothermal storage) after coating.

While this instability problem is known not to exist when the polymers are applied from organic solvent solution, it has not been possible to obtain a controlled release formulation utilizing coatings prepared from such aqueous acrylic polymer dispersions which is stable under various storage conditions.

In particular, it is known that controlled release coatings of commercially available acrylic polymers such as those sold under the tradename Eudragit® by Rohm Pharma GmbH are not stable when cured according to recommended curing conditions of 45° C. for 2 hours.

OBJECTS AND SUMMARY OF THE INVENTION

It is therefore an object of the present invention to provide a controlled release formulation of a substrate comprising an active agent, e.g. a therapeutically active agent, a disinfecting agent, a cleansing agent, a sanitizing agent and a fertilizing agent, coated with an aqueous dispersion of a hydrophobic acrylic polymer such that there is a stable dissolution or other release profile of the active agent when placed in an environment of use, despite exposure to a variety of storage conditions, including accelerated storage conditions.

It is another object of the present invention to provide a controlled release formulation comprising a plurality of inert beads comprising an active agent, and a controlled release tablet comprising a core containing an active agent, the beads or tablet core being coated with an aqueous dispersion of a hydrophobic polymer and providing a reproducible, stable dissolution despite exposure to accelerated storage conditions, as well as a method of preparing the same.

Still another object of the present invention is to provide a controlled release formulation comprising a substrate containing an active agent coated with an aqueous dispersion of a hydrophobic polymer which upon dissolution in-vitro provides a band range, when comparing the dissolution profile of the formulation after exposure to a variety of storage conditions including "stressed" or accelerated storage conditions, which is not wider than about 15% of total active agent released at any point of time during the dissolution.

A further object of the present invention is to provide a controlled release formulation wherein the controlled release is caused by a coating on the formulation of an aqueous dispersion of a hydrophobic polymer such as an acrylic polymer which coating provides a stable dissolution of an active agent contained in the formulation, despite exposure to accelerated storage conditions such that the dissolution would be deemed acceptable by a governmental regulatory agency such as the U.S. FDA for purposes' of according expiration dating.

These objects and others have been accomplished by the present invention, which relates in part to a controlled release formulation comprising a substrate comprising an active agent in an amount sufficient to provide a desired effect in an environment of use, the substrate being coated with an aqueous dispersion of plasticized pharmaceutically acceptable hydrophobic acrylic polymer in an amount sufficient to obtain a controlled release of said active agent when said formulation is exposed to an environmental fluid, and cured at a temperature greater than the glass transition temperature of the aqueous dispersion of plasticized acrylic polymer for a sufficient period of time until a curing endpoint is reached at which the coated substrate provides a stable dissolution of the active agent which is unchanged after exposure to accelerated storage conditions. The endpoint may be determined, e.g., by comparing the dissolution profile of the formulation immediately after curing to the dissolution profile of the formulation after exposure to accelerated storage conditions such as one to three months at a temperature of 37° C. and at a relative humidity of 80%, or at a temperature of 40° C. and at a relative humidity of 75%. In certain preferred embodiments, the substrate is coated to a weight gain from about 2% to about 25%.

In other preferred embodiments, the coated substrate when subjected to in-vitro dissolution, releases said active agent in amounts which do not vary at any time point along the dissolution curve by more than about 15% of the total amount of active agent released, when compared to the in-vitro dissolution of said coated substrate after curing.

In yet other embodiments of the invention, the cured formulation provides a stabilized dissolution of said active agent which is unchanged after exposure to accelerated storage conditions, the stabilized dissolution being deemed appropriate by the United States Food & Drug Administration for the purpose of according expiration dating for said formulation.

Other preferred embodiments relate to controlled release dosage formulation comprising a substrate coated with an effective amount of an aqueous dispersion of acrylic polymer to obtain a controlled release of an active agent which formulation, after exposure to accelerated storage conditions, releases an amount of therapeutically active agent which does not vary at any given dissolution time point by more than about 20% of the total amount of therapeutically active agent released, when compared to in-vitro dissolution conducted prior to storage. The acrylic polymer preferably has a permeability which is unaffected by the pH conditions prevailing in the gastrointestinal tract.

In other embodiments, the coated substrate, upon in-vitro dissolution testing, provides a band range after exposure to accelerated storage conditions which is not wider than about 20% at any point of time when compared to the dissolution profile prior to exposure to the accelerated storage conditions.

The active agent may be chosen for a wide variety of uses, including but not limited to systemically active therapeutic agents, locally active therapeutic agents, disinfectants, cleansing agents, fragrances, fertilizers, deodorants, dyes, animal repellents, insect repellents, pesticides, herbicides, fungicides, and plant growth stimulants.

The present invention is further related to a solid controlled release oral dosage formulation, comprising a substrate containing a systemically active therapeutic agent in an amount sufficient to provide a desired therapeutic effect when said formulation is orally administered. The substrate is coated with an aqueous dispersion of plasticized acrylic polymer and cured at a temperature greater than the glass transition temperature of the aqueous dispersion of plasticized acrylic polymer for a period of time sufficient to obtain a controlled release of said active agent when measured by the USP Paddle or Basket Method at 100 rpm at 900 ml aqueous buffer (pH between 1.6 and 7.2) at 37° C. from about 0% to about 42.5% (by wt) active agent released after 1 hour, from about 5% to about 60% (by wt) active agent released after 2 hours, from about 15% to about 75% (by wt) active agent released after 4 hours, and from about 20% to about 90% (by wt) active agent released after 8 hours. The coated substrate has a stable release when comparing the rate of release of the active agent after exposing the coated substrate to accelerated conditions, to the release rate obtained immediately after curing. The dosage form preferably provides a therapeutic effect for about 24 hours. The present invention further relates to a method of preparing the dosage form.

The present invention is also related to a method for obtaining a controlled release formulation of an active agent, comprising preparing a solid substrate comprising an active agent, coating the substrate with a sufficient amount an aqueous dispersion of plasticized acrylic polymer to obtain a predetermined controlled release of the active agent when the coated substrate is exposed to an environmental fluid, and curing the coated substrate at a temperature greater than the glass transition temperature of the aqueous dispersion of plasticized acrylic polymer until a curing endpoint is reached at which said coated substrate provides a stabilized dissolution of said active agent which is unchanged after exposure to accelerated storage conditions.

The present invention is further related to a method of treating a patient with an oral solid dosage form described above. In this method, present invention further comprises administering the oral solid dosage form comprising the cured, coated substrate to the patient to thereby obtain the desired therapeutic effect for about 12 to about 24 hours or more. In especially preferred embodiments, the oral solid dosage forms of the present invention provide a desired therapeutic effect for about 24 hours.

In certain preferred embodiments of the present invention, the hydrophobic acrylic polymer is comprised of copolymerizates of acrylic and methacrylic acid esters having a permeability which is unaffected by the pH conditions prevailing in the gastrointestinal tract. Preferably, these copolymerizates further include a low content of quaternary ammonium groups, which occur as salts and are responsible for the permeability of the lacquer substances.

The present invention provides many benefits over prior art coatings, including, but not limited to, avoidance of organic solvents which have inherent safety concerns (flammability, carcinogenicity, environmental concerns, cost, safety in general), and extended stability which may result in extended shelf life and expiration dating.

BRIEF DESCRIPTION OF THE DRAWINGS

The following drawings are illustrative of embodiments of the invention and are not meant to limit the scope of the invention as encompassed by the claims.

DETAILED DESCRIPTION

Figure 1:
FIG. 1 is a graphical representation of the dissolution results of Comparative Example 13A.

The aqueous dispersions of hydrophobic acrylic polymers used as coatings in the present invention may be used to coat substrates such as tablets, spheroids (or beads), microspheres, seeds, pellets, ion-exchange resin beads, and other multi-particulate systems in order to obtain a desired controlled release of the active agent. Granules, spheroids, or pellets, etc., prepared in accordance with the present invention can be presented in a capsule or in any other suitable dosage form. The tablets of the present invention may be any suitable shape, such as round, oval, biconcave, hemispherical, any polygonal shape such as square, rectangular, and pentagonal, and the like.

In order to obtain a controlled release formulation, it is usually necessary to overcoat the substrate comprising the active agent with a sufficient amount of the aqueous dispersion of hydrophobic acrylic polymer to obtain a weight gain level from about 2 to about 25 percent, although the overcoat may be lesser or greater depending upon the physical properties of the active agent and the desired release rate, the inclusion of plasticizer in the aqueous dispersion and the manner of incorporation of the same, for example. In certain embodiments of the invention, the controlled release coatings may be applied to the substrate up to, e.g., a 50% weight gain.

The cured, coated substrates of the present invention provide a stable dissolution profile (e.g., release of the active agent in the environment of use) when stored for extended periods of time at room temperature and ambient humidity (e.g., long term (real time) testing), and when tested under accelerated storage conditions.

The terms "stable dissolution profile" and "curing endpoint" are defined for purposes of the present invention as meaning that the cured, coated substrate reproducibly provides a release of the active agent when placed in an environment of use which is unchanged, even after exposing the cured, coated substrate to accelerated storage conditions. Those skilled in the art will recognize that by "unchanged" it is meant that any change in the release of the active agent from the cured, coated formulation would be deemed insignificant in terms of the desired effect. For pharmaceutical formulations, stability is evaluated by, e.g., a regulatory agency such as the Food & Drug Administration (FdA) in the U.S., for the purpose of according an expiration date for the formulation.

By the phrase "accelerated storage conditions" it is meant, e.g., storage conditions of elevated temperature and/or elevated relative humidity. Preferably, the phrase "accelerated storage conditions" refers-to storage conditions to which the final drug formulation is subjected for the purpose of obtaining regulatory approval (e.g., FDA approval in the U.S.) and an expiration date.

The term "expiration date" is defined for purposes of the present invention as the date designating the time during which a packaged batch of the product (e.g., the cured, coated substrate) is expected to remain within specification if stored under defined conditions, and after which it should not be used.

By "environmental fluid", it is meant that the formulation is placed in an aqueous solution (e.g., in-vitro dissolution), in simulated gastric fluid (e.g., in accordance with the USP Basket Method (i.e., 37° C., 100 RPM, first hour 700 ml gastric fluid with or without enzymes at pH 1.2, then changed to 900 ml at pH 7.5), or in gastrointestinal fluid (in-vivo).

The term "band range" or "band width" for purposes of the present invention is defined as the difference in in-vitro dissolution measurements of the controlled release formulations when comparing the dissolution profile (curve) obtained by the formulation upon completion of the manufacturing of the coated product (prior to storage) and the dissolution profile obtained after the coated product is exposed to accelerated storage conditions, expressed as the total (absolute) change in percent of the active agent released from the coated product at any dissolution time point along the dissolution curves.

In general, the length of the studies and the storage test conditions required by regulatory agencies such as the FDA for pharmaceutical formulations are sufficient to cover storage, shipment, and subsequent use. Allowable storage test conditions may vary depending upon the particulars of the product. For example, temperature sensitive drug substances should be stored under an alternative, lower temperature condition, which is then deemed to be the long term testing storage temperature. In such cases, it is generally accepted that the accelerated testing should be carried out at a temperature at least 15° C. above this designated long term storage temperature, together with appropriate relative humidity conditions for that temperature.

A generally accepted accelerated test employed in FDA guidelines relates to the storage of a drug product (e.g., in its container and package) at 80% Relative Humidity (RH) and 37° C. (1985 FDA guidelines). If the product holds up for, e.g., three months under these conditions (chemical stability, dissolution, and physical characteristics), then the drug product will be accorded, e.g., a two year expiration date. This accelerated test is also now also considered to be acceptable if conducted at 75% RH and 40° C. (FDA 1987 guidelines). It has recently been proposed that long-term storage testing be conducted for pharmaceutical formulations at 25° C.±2° C. at not less than 60% RH±5% for a minimum time period of 12 months. It has been further proposed that accelerated testing be conducted for pharmaceutical formulations at 40° C.±2° C. at 75% RH±5% for a minimum time period of 6 months. All of the above-mentioned accelerated testing criteria and others are deemed equivalent for purposes of the present invention, with regard to the determination of stability and the determination of the curing endpoint. All of the above-mentioned accelerated testing conditions, as well as others known to those skilled in the art, provide an acceptable basis for determining the curing (stability) endpoint of the controlled release formulations of the present invention.

The controlled release coatings of the present invention comprise aqueous dispersions of hydrophobic (water-insoluble) acrylic polymers. In certain preferred embodiments, the hydrophobic acrylic polymer coatings of the present invention have a solubility and permeability independent of the pH of the fluid present in the environment of use. In the case of oral solid dosage forms, the hydrophobic acrylic polymers of the present invention have a solubility and permeability independent of physiological pH values. Hydrophobic acrylic polymers which may be used in the formulations of the present invention are derived from acrylic acid or derivatives thereof. Acrylic acid derivatives include, for example, the esters of acrylic acid and methacrylic acid, and the alkyl esters of acrylic acid and methacrylic acid. In certain preferred embodiments, the alkyl esters of acrylic acid and methacrylic acid have from about 1 to about 8 carbon atoms in the alkyl group. The monomers which may be used in the polymer coatings of the present invention also include styrene and its homologs, vinyl esters such as vinyl acetate, and vinyl chloride. Generally, monomers forming hydrophobic water-insoluble polymers are nonionic. The term "non-ionic monomers" for purposes of the present invention is meant to include not only monomers which have no ionic groups (such as alkali metal carboxylate or sulfonate or tertammonium groups) in the molecule, but also monomers which are unable to form such groups with bases or acids. In many cases, the composition of the hydrophobic acrylic polymer coating may include other monomers.

One skilled in the art will appreciate that the hardness and extensibility of the coating film and the lowest temperature at which film formation from the aqueous dispersion is possible are influenced by the particular monomers included in the hydrophobic acrylic polymer used in the present invention. Lower alkyl esters of methacrylid acid are known to form relatively harder homopolymers, which acrylic acid esters and the higher alkyl esters of methacrylic acid provide relatively softer homopolymers. Alkyl groups having greater than 4 carbon atoms or aryl groups have a hydrophobizing effect and thereby reduce the swelling capacity and diffusion permeability.

In certain preferred embodiments of the present invention, the acrylic polymer also includes one or more polymerizable permeability-enhancing compounds which will allow the active agent enclosed within the coating to be released at a desired diffusion rate, regardless of the prevailing pH value. In the case of oral solid dosage forms, the permeability-enhancing compound allows the active agent to be released at the same diffusion rate in each region of the digestive (gastrointestinal) tract (regardless of pH) during passage of the dosage form therethrough; after having been substantially completely extracted, the coatings of the present invention are eliminated without decomposing.

In certain preferred embodiments, the permeability-enhancing compound comprises at least one polymerizable quaternary ammonium compound. Such compounds are strong bases which are present as stable salts in a wide pH range, e.g., throughout the entire physiological pH region, and are easily water soluble. The nature, and particularly the amount, of the quaternary ammonium compound present in the copolymeric agent are important factors affecting diffusion behavior.

Suitable polymerizable quaternary ammonium compounds which may be used in the coatings of the present invention generally correspond to the general formula

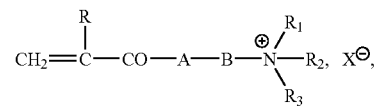

wherein
R is hydrogen or methyl; A is oxygen or NH; B is a linear or branched alkyl or is an alicyclic hydrocarbon, preferably having from about 2 to about 8 carbon atoms; $R_1$, $R_2$ and $R_3$, taken alone, are the same or different alkyl or aralkyl, and more particularly are lower alkyl having from about 1 to about 4 carbon atoms, or are benzyl, or R1 and R2, taken together with the quaternary nitrogen atom, are piperidinium or morpholinium; and
$X^\ominus$ is a cation, preferably of an inorganic acid, particularly chloride, sulfate, or methosulfate.

Particular examples of polymerizable quaternary ammonium compounds include quaternized aminoalkyl esters and aminoalkyl amides of acrylic acid and methacrylic acid, for example β-methacryl-oxyethyl-trimethyl-ammonium methosulfate, β-acryloxy-propyl-trimethyl-ammonium chloride, and trimethylaminomethylmethacrylamide methosulfate. The quaternary ammonium atom can also be part of a heterocycle, as in methacryloxyethylmethyl-morpholinium chloride or the corresponding piperidinium salt, or it can be joined to an acrylic acid group or a methacrylic acid group by way of a group containing hetero atoms, such as a polyglycol ether group. Further suitable polymerizable quaternary ammonium compounds include quaternized vinyl-substituted nitrogen heterocycles such as methyl-vinyl pyridinium salts, vinyl esters of quaternized amino carboxylic acids, styryltrialkyl ammonium salts, and the like.

Other polymerizable quaternary ammonium compounds useful in the present invention are acryl- and methacryl-oxyethyltrimethylammonium chloride and methosulfate, benzyldimethylammoniumethylmethacrylate chloride, diethylmethylammoniumethyl-acrylate and -methacrylate methosulfate, N-trimetliylammoniumpropylmethacrylamide chloride, and N-trimethylammonium-2,2-dimethylpropyl-1-methacrylate chloride.

Further information concerning suitable hydrophobic acrylic polymers may be obtained from U.S. Pat. Nos. 3,520,970 and 4,737,357 (both assigned to Rohm G.m.b.H), both of which are hereby incorporated by reference.

One skilled in the art will appreciate that other polymerizabilable permeability-enhancing compounds may be substituted in the present invention for the quaternary ammonium compounds mentioned above. Such additional polymerizable permeability-enhancing compounds are contemplated to be within the scope of the appended claims.

In certain preferred embodiments, the hydrophobic acrylic polymer used in the coatings of the present invention comprises copolymerizates of acrylic and methacrylic acid esters with a low content of quaternary ammonium groups. Such copolymerizates are often referred to as ammonio methacrylate copolymers, and are commercially available from Rohm Pharma AG, e.g., under the tradename Eudragit®. Ammonio methacrylate copolymers are described in NF XVII as fully polymerized copolymers of acrylic and methacrylic acid esters with a low content of quaternary ammonium groups.

In certain especially preferred embodiments of the present invention, the acrylic coating is derived from a mixture of two acrylic resin lacquers used in the form of aqueous dispersions, commercially available from Rohm Pharma under the Tradename Eudragit® RL 30 D and Eudragit® RS 30 D, respectively. Eudragit® RL 30 D and Eudragit® RS 30 D are copolymers of acrylic and methacrylic esters with a low content of quaternary ammonium groups, the molar ratio of ammonium groups to the remaining neutral (meth) acrylic esters being 1:20 in Eudragit® RL 30 D and 1:40 in Eudragit® RS 30 D. The mean molecular weight is about 150,000. The code designations refer to the permeability properties of these agents, RL for high permeability and RS for low permeability. Eudragit® RL/RS mixtures are insoluble in water and in digestive fluids. However, coatings formed from the same are swellable and permeable in aqueous solutions and digestive fluids.

The Eudragit® RL/RS dispersions of the present invention may be mixed together in any desired ratio in order to ultimately obtain a controlled release formulation having a desirable dissolution profile. Desirable controlled release formulations may be obtained, for instance, from a retardant coating derived from 100% Eudragit® RL, 50% Eudragit® RL and 50% Eudragit® RS, and 10% Eudragit® RL:Eudragit® 90% RS, and 100% Eudragit® RS.

The hydrophilic acrylic polymers used in the present invention may be manufactured in any manner known to those skilled in the art, including methods such as bulk polymerization in the presence of a free radical-forming initiator dissolved in the monomer mixture, or solution or precipitation polymerization in an organic solvent, with the polymer thus formed thereafter being isolated from the solvent.

The hydrophobic acrylic polymer coatings of the present invention may also include hydrophilic monomers having a solubility which is not dependent on pH. Examples are acrylamide and methacrylamide, hydroxy alkyl esters of acrylic acid and methacrylic acid, and vinyl pyrrolidone. Such materials if used, may be included in small amounts up to 20 percent by weight of the copolymer. Also, small amounts of ionic monomers, such as acrylic acid or methacrylic acid or amino monomers on which the quaternized monomers are based, may also be included.

In other embodiments of the present invention, the hydrophobic acrylic polymer coating further includes a polymer whose permeability is pH dependent, such as anionic polymers synthesized from methacrylic acid and methacrylic acid methyl ester. Such polymers are commercially available, e.g., from Rohm Pharma GmbH under the tradename Eudragit® L and Eudragit® S. The ratio of free carboxyl groups to the esters is said to be 1:1 in Eudragit® L and 1:2 in Eudragit® S. Eudragit® L is insoluble in acids and pure water, but becomes increasingly permeable above pH 5.0. Eudragit® S is similar, except that it becomes increasingly permeable above pH 7. The hydrophobic acrylic polymer coatings may also include a polymer which is cationic in character based on dimethylaminoethyl methacrylate and neutral methacrylic acid esters (such as Eudragit® E, commercially available from Rohm Pharma). The hydrophobic acrylic polymer coatings of the present invention may further include a neutral copolymer based on poly (meth) acrylates, such as Eudragit® NE (NE=neutral ester), commercially available from Rohm Pharma. Eudragit® NE 30D lacquer films are insoluble in water and digestive fluids, but permeable and swellable.

The dissolution profile of any given formulation in accordance with the present invention may by altered by changing the relative amounts of different acrylic resin lacquers included in the coating. Also, by changing the molar ratio of polymerizable permeability-enhancing agent (e.g., the quaternary ammonium compounds) to the neutral (meth)acrylic esters, the permeability properties (and thus the dissolution profile) of the resultant coating can be modified.

The release of the active agent from the controlled release formulation of the present invention can be further influenced, i.e., adjusted to a desired-rate, by the addition of one or more pore-formers which can be inorganic or organic, and include materials that can be dissolved, extracted or leached from the coating in the environment of use. Upon exposure to fluids in the environment of use, the pore-formers are, e.g., dissolved, and channels and pores are formed that fill with the environmental fluid.

For example, the pore-formers may comprise one or more water-soluble hydrophilic polymers in order to modify the release characteristics of the formulation. Examples of suitable hydrophilic polymers include hydroxypropylmethylcellulose, cellulose ethers and protein-derived materials. Of these polymers, the cellulose ethers, especially hydroxyalkylcelluloses and carboxyalkylcelluloses, are preferred. Also, synthetic water-soluble polymers may be used, such as polyvinylpyrrolidone, cross-linked polyvinylpyrrolidone, polyethylene oxide, etc., water-soluble polydextrose, saccharides and polysaccharides, such as pullulan, dextran, sucrose, glucose, fructose, mannitol, lactose, mannose, galactose, sorbitol and the like In certain preferred embodiments of the present invention, the hydrophilic polymer comprises hydroxypropylmethylcellulose.

Other examples of pore-formers include alkali metal salts such as lithium carbonate, sodium chloride, sodium bromide, potassium chloride, potassium sulfate, potassium phosphate, sodium acetate, sodium citrate, and the like. The pore-forming solids may also be polymers which are soluble in the environment of use, such as Carbowaxes®, Carbopol®, and the like. The pore-formers embrace diols, polyols, polyhydric alcohols, polyalkylene glycols, polyglycols, poly(a-w)alkylenediols, and the like.

Semipermeable polymers may also be incorporated in the controlled release coating as a pore-former to change the release characteristics of the formulation. Such semipermeable polymers include, for example, cellulose acylates, acetates, and other semi-permeable polymers such as those described in U.S. Pat. No. 4,285,987 (hereby incorporated by reference), as well as the selectively permeable polymers formed by the coprecipitation of a polycation and a polyanion as disclosed in U.S. Pat. Nos. 3,173,876; 3,276,586; 3,541,005; 3,541,006 and 3,546,142 (hereby incorporated by reference).

Other pore-formers which may be useful in the formulations of the present invention include starch, modified starch, and starch derivatives, gums, including but not limited to xanthan gum, alginic acid, other alginates, bentonite, veegum, agar, guar, locust bean gum, gum arabic, quince psyllium, flax seed, okra gum, arabinoglactin, pectin, tragacanth, scleroglucan, dextran, amylose, amylopectin, dextrin, etc., cross-linked polyvinylpyrrolidone, ion-exchange resins, sucH as potassium polymethacrylate, carrageenan, kappa-carrageenan, lambdacarrageenan, gum karaya, biosynthetic gum, etc. Other pore-formers include materials useful for making microporous lamina in the environment of use, such as polycarbonates comprised of linear polyesters of carbonic acid in which carbonate groups reoccur in the polymer chain, microporous materials such as bisphenol, a microporous poly(vinylchloride), microporous polyamides, microporous modacrylic copolymers, microporous styrene-acrylic and its copolymers, porous polysulfones, halogenated poly(vinylidene), polychloroethers, acetal polymers, polyesters prepared by esterification of a dicarboxylic acid or anhydride with an alkylene polyol, poly(alkylenesulfides), phenolics, polyesters, asymmetric porous polymers, cross-linked olefin polymers, hydrophilic microporous homopolymers, copolymers or interpolymers having a reduced bulk density, and other similar materials, poly(urethane), cross-linked chain-extended poly(urethane), poly(imides), poly(benzimidazoles), collodion, regenerated proteins, semi-solid cross-linked poly(vinylpyrrolidone).

In general, the amount of pore-former included in the controlled release coatings of the present invention may be from about 0.1% to about 80%, by weight, relative to the combined weight of hydrophobic acrylic polymer and pore-former.

The controlled release coatings of the present invention may also include an exit means comprising at least one passageway, orifice, or the like. The passageway may be formed by such methods as those disclosed in U.S. Pat. Nos. 3,845,770; 3,916,889; 4,063,064; and 4,088,864 (all of which are hereby incorporated by reference). The passageway can have any shape such as round, triangular, square, elliptical, irregular, etc. The passageway may be included instead of, or in addition to, the inclusion of permeability-enhancing compounds, hydrophilic monomers, pH-sensitive polymers, and/or pore-formers, in order to obtain a release of the active agent(s) included in the formulation.

In one embodiment of the present invention, the hydrophobic polymer included in the aqueous polymer coating dispersion is water-insoluble (such as a copolymer of acrylic and methacrylic acid esters without the inclusion of any quaternary ammonium compound), and the release of the active agent is controlled substantially only via the presence of one or more passageways through the coating.

An example of a suitable controlled release formulation pursuant to the present invention will provide a dissolution rate in vitro of the dosage form, when measured by the USP Paddle or Basket Method at 100 rpm in 900 ml aqueous buffer (pH between 1.6 and 7.2) at 37° C., is from about 0 to about 42.5% (by wt) therapeutically active agent released after 1 hour, from about 25 from about 55% (by wt) released after 2 hours, between 45 and 75% (by wt) released after 4 hours and greater than about 55% (by wt) released after 6 hours, for, e.g., a 12 hour formulation (administered twice daily). Another example of a suitable controlled release formulation pursuant to the present invention is one which will provide a dissolution rate in vitro of the dosage form, when measured by the USP Paddle or Basket Method at 100 rpm at 900 ml aqueous buffer (pH between 1.6 and 7.2) at 37° C. from about 0% to about 42.5% (by wt) active agent released after 1 hour, from about 5% to about 60% (by wt) active agent released after 2 hours, from about 15% to about 75% (by wt) active agent released after 4 hours, and from about 20% to about 90% (by wt) active agent released after 8 hours, for e.g., a 24 hour formulation (administered once daily). These examples of acceptable dissolution rates are directed to certain preferred embodiments of the present invention where the formulations are oral solid dosage forms, and are not intended to be limiting in any manner whatsoever.

The coating formulations of the present invention should be capable of producing a strong, continuous film that is smooth and elegant, capable of supporting pigments and other coating additives, non-toxic, inert, and tack-free.

It is preferred that the acrylic coatings used in the present invention include an effective amount of a suitable plasticizing agent, as it has been found that the use of a plasticizer further improves the physical properties of the film. For example, the use of a plasticizer may improve the film elasticity and lower the film-forming temperature of the dispersion. The plasticization of the acrylic resin may be accomplished either by so-called "internal plasticization" and "external plasticization."

Internal plasticization usually pertains directly to molecular modifications of the polymer during its manufacture, e.g., by copolymerization, such as altering and/or substituting functional groups, controlling the number of side chains, or controlling the length of the polymer. Such techniques are usually not performed by the formulator of the coating solution.

External plasticization involves the addition of a material to a film solution so that the requisite changes in film properties of the dry film can be achieved.

The suitability of a plasticizer depends on its affinity or solvating power for the polymer and its effectiveness at interfering with polymer-polymer attachments. Such activity imparts the desired flexibility by relieving molecular rigidity. Generally, the amount of plasticizer included in a coating solution is based on the concentration of the film-former, e.g., most often from about 1 to about 50 percent by weight of the film-former. Concentration of the plasticizer, however, can only be properly determined after careful experimentation with the particular coating solution and method of application.

Most preferably, about 20% plasticizer is included in the aqueous dispersion of acrylic polymer.

An important parameter in the determination of a suitable plasticizer for a polymer is related to the glass transition temperature (Tg) of the polymer. The glass transition temperature is related to the temperature or temperature range where there is a fundamental change in the physical properties of the polymer. This change does not reflect a change in state, but rather a change in the macromolecular mobility of the polymer. Below the Tg, the polymer chain mobility is severely restricted. Thus, for a given polymer, if its Tg is above room temperature, the polymer will behave as a glass, being hard, non-pliable and rather brittle, properties which could be somewhat restrictive in film coating since the coated dosage form may be subjected to a certain amount of external stress.

Incorporation of suitable plasticizers into the polymer matrix effectively reduces the Tg, so that under ambient conditions the films are softer, more pliable and often stronger, and thus better able to resist mechanical stress.

Other aspects of suitable plasticizers include the ability of the plasticizer to act as a good "swelling agent" for the acrylic resin.

Examples of suitable plasticizers for the acrylic polymers of the present invention include, but are not limited to citric acid esters such as triethyl citrate NF XVI, tributyl citrate, dibutyl phthalate, and possibly 1,2-propylene glycol. Other plasticizers which have proved to be suitable for enhancing the elasticity of the films formed from acrylic films such as Eudragit® RL/RS lacquer solutions include polyethylene glycols, propylene glycol, diethyl phthalate, castor oil, and triacetin. Triethyl citrate is an especially preferred plasticizer for the aqueous dispersions of acrylic polymers of the present invention.

It has further been found that the addition of a small amount of talc reduces the tendency of the aqueous dispersion to stick during processing, and acts as a polishing agent.

The dissolution profile of the ultimate product may also be modified, for example, by increasing or decreasing the thickness of the retardant coating, by altering the manner in which the plasticizer is added, by varying the amount of plasticizer relative to acrylic resin, and/or by altering other aspects of the method of manufacture, for example.

In one preferred embodiment of the present invention, the controlled release dosage form comprises pharmaceutically acceptable beads (e.g., spheroids) containing the active ingredient coated with a controlled release coating. The term spheroid is known in the pharmaceutical art and means, e.g., a spherical granule having a diameter of between 0.2 mm and 2.5 mm especially between 0.5 mm and 2 mm. A suitable commercially available example of such beads are nu pariel 18/20 beads.

A plurality of the cured, coated (stabilized) controlled release beads may thereafter be placed in a gelatin capsule in an amount sufficient to provide an effective controlled release dose when ingested and contacted by gastric fluid.

When the dispersion of acrylic resin is used to coat inert pharmaceutical beads such as nu pariel 18/20 mesh beads, a plurality of the resultant stabilized solid controlled release beads may thereafter be placed in a gelatin capsule in an amount sufficient to provide an effective controlled release dose when ingested and contacted by gastric fluid. In this embodiment, beads coated with a therapeutically active agent are prepared, e.g., by dissolving the therapeutically active agent in water and then spraying the solution onto a substrate, for example, nu pariel 18/20 mesh beads, using a Wurster insert. Optionally, additional ingredients are also added prior to coating the beads in order to assist the active ingredient binding to the beads, and/or to color the solution, etc. For example, a product which includes hydroxypropyl methylcellulose, etc. with or without colorant may be added to the solution and the solution mixed (e.g., for about 1 hour) prior to application of the same onto the beads. The resultant coated substrate, in this example beads, may then be optionally overcoated with a barrier agent, to separate the therapeutically active agent from the acrylic coating. An example of a suitable barrier agent is one which comprises hydroxypropyl methylcellulose. However, any film-former known in the art may be used. It is preferred that the barrier agent does not affect the dissolution rate of the final product.

The beads comprising the active agent (with optional protective coating) may then be overcoated with the acrylic polymer. The dispersion of acrylic polymer preferably further includes an effective amount of plasticizer, e.g. triethyl citrate. Pre-formulated dispersions of acrylic resins, such as various commercially available forms of Eudragit®, such as Eudragit® RS30D and Eudragit® RL 30D.

The coating solutions of the present invention preferably contain, in addition to the film-former, plasticizer, and solvent system (i.e., water), a colorant to provide elegance and product distinction. Color may be added to the solution of the therapeutically active agent instead, or in addition to the overcoat. Suitable ingredients for providing color to the formulation include titanium dioxide and color pigments, such as iron oxide pigments. The incorporation of pigments, may, however, increase the retard effect of the coating. Alternatively, any suitable method of providing color to the formulations of the present invention may be used.

The plasticized coating of acrylic polymer (with optional permeability enhancing compounds and/or pore-formers) may be applied onto the substrate comprising the therapeutically active agent by spraying using any suitable spray equipment known in the art. In a preferred method, a Wurster fluidized-bed system is used in which an air jet, injected from underneath, fluidizes the core material and effects drying while the acrylic polymer coating is sprayed on. A sufficient amount of the coating to obtain a predetermined controlled release of the therapeutically active agent when said coated substrate is exposed to aqueous solutions, e.g. gastric fluid, is preferably applied, taking into account the physical characteristics of the therapeutically active agent, the manner of incorporation of the plasticizer, etc. After coating with acrylic resin., a further overcoat of a film-former, such as Opadry®, is optionally applied to the beads. This overcoat is provided, if at all, in order to substantially reduce agglomeration of the beads.

Next, the coated beads, tablets, etc. are cured in order to obtain a stabilized release rate of the therapeutically active agent.

Traditionally, curing has been carried out for Eudragit® coated formulations, if at all, via a fluid bed at 45° C. for 2 hours after application. Such a standard curing is recommended by Rohm Pharma because it is above the glass transition temperature (Tg) of Eudragit® RS 30 D plasticized with triethylcitrate at a 20% level of solids. This recommended curing does not stabilize the dissolution profile of the formulation upon storage, as will be demonstrated by the examples set forth herein.

The curing step pursuant to the present invention is accomplished by subjecting the coated substrate, e.g., beads, to a temperature greater than the Tg of the coating formulation and continuing the curing until an endpoint is reached at which the coated formulation attains a dissolution profile which is substantially unaffected by exposure to storage conditions of elevated temperature and/or humidity. Generally, the curing time is about 24 hours or more, and the curing temperature may be, for example, about 45° C. It has further been discovered in the present invention that it is not necessary to subject the coated substrate to humidity levels above ambient conditions during the curing step in order to achieve a stabilized end product.

One possible mechanism for the change in the dissolution profile of prior art products cured by the standard methods is that these products continue to cure during storage, and may never reach a stabilized end-point at which the product provides a substantially constant dissolution profile. In contrast, the cured products of the present invention provide a release rate of the therapeutically active agent which is substantially unaffected during storage by elevations in temperature and humidity.

In preferred embodiments of the present invention, the stabilized product is obtained by subjecting the coated substrate to oven curing at a temperature above the Tg of the plasticized acrylic polymer for the required time period, the optimum values for temperature and time for the particular formulation being determined experimentally.

In certain embodiments of the present invention, the stabilized product is obtained via an oven curing conducted at a temperature of about 45° C. for a time period from about 24 to about 48 hours. In certain embodiments, it may be preferable to cure the product for, e.g., 36 hours. In certain preferred embodiments, the product is cured for about 48 hours. It is also contemplated herein that certain products coated with the controlled release coating of the present invention may require a curing time longer than 48 hours, e.g. 60 hours or more. One skilled in the art will recognize that curing conditions will be affected by the particular drug incorporated in the formulation, as well as by the thickness of the controlled release coating, and the size of the substrate (e.g., beads as compared to tablets).

It is especially contemplated that the time period needed for curing to an endpoint as described above may actually be longer or shorter than the time periods mentioned above. Such curing times which achieve the intended result of a stabilized formulation are considered to be encompassed by the appended claims. Additionally, it will be appreciated by those skilled in the art that it may be possible to cure the aqueous dispersion coated substrates of the present invention in other manners in order to reach the endpoint at which the coated substrate provides a stable dissolution profile. Additional curing methods (such as sonication) which achieve the intended result of a stabilized formulation are also considered to be encompassed by the appended claims.

The curing endpoint may be determined by comparing the dissolution profile of the cured, coated substrate (e.g., the "formulation") immediately after curing (hereinafter referred to as "the initial dissolution profile") to the dissolution profile of the formulation after exposure to accelerated storage conditions. Generally, the curing endpoint may be determined by comparing the dissolution profile of the formulation after exposure to accelerated storage conditions of, e.g., 37° C./80% RH or 40° C./75% RH for a time period of one month to the initial dissolution profile. However, the curing endpoint may be further confirmed by continuing to expose the cured, coated formulation to accelerated storage conditions for a further period of time and comparing the dissolution profile of the formulation after further exposure of, e.g., two months and/or three months, to the initial dissolution profile obtained.

In certain preferred embodiments of the present invention in which the cured coated substrate is a pharmaceutical formulation, the curing endpoint is attained when the data points plotted along a graph of the dissolution curve obtained after, e.g., exposure to accelerated conditions of 1–3 months, show a release of the active agent which does not vary at any given time point by more than about 15% of the total amount of active agent released when compared to in-vitro dissolution conducted prior to storage. Such a difference in the in-vitro dissolution curves, referred to in the art as a "band range" or a "band width" of, e.g., 15%. In general, where the in-vitro dissolution prior to storage and after exposure to accelerated conditions varies by not more than, e.g., about 20% of the total amount of active agent released, the formulation is considered acceptable when considered by governmental regulatory agencies such as the U.S. FDA for stability concerns and expiration dating. Acceptable band ranges are determined by the FDA on a case-by-case basis, and any band range for a particular pharmaceutical which would be deemed acceptable by such a governmental regulatory agency would be considered to fall within the appended claims. In preferred embodiments, the aforementioned band range is not more than 10% of the total amount of active agent released. In more preferred embodiments, the band range is not more than 7% of the total amount of active agent released. In the appended Examples, the band range is often less than 5%.

When the controlled release coating of the present invention is to be applied to tablets, the tablet core (e.g. the substrate) may comprise the active agent along with any pharmaceutically accepted inert pharmaceutical filler (diluent) material, including but not limited to sucrose, dextrose, lactose, microcrystalline cellulose, xylitol, fructose, sorbitol, mixtures thereof and the like. Also, an effective amount of any generally accepted pharmaceutical lubricant, including the calcium or magnesium soaps may be added to the above-mentioned agents of the excipient prior to compression of the tablet core agents. Most preferred is magnesium stearate in an amount of about 0.2–5% by weight of the solid dosage form.

In certain embodiments of the present invention, the coated substrate includes an additional dose of active agent included in either the controlled release coating comprising the aqueous dispersion of hydrophobic polymer, or in an additional overcoating coated on the outer surface of the controlled release coating. This may be desired when, for example, a loading dose of a therapeutically active agent is needed to provide therapeutically effective blood levels of the active agent when the formulation is first exposed to gastric fluid. In such cases, a further protective coating (e.g., of HPMC) may be included to separate the immediate release coating layer from the controlled release coating layer.

The active agent(s) included in the controlled release formulations of the present invention include systemically active therapeutic agents, locally active therapeutic agents, disinfecting agents, chemical impregnants, cleansing agents, deodorants, fragrances, dyes, animal repellents, insect repellents, a fertilizing agents, pesticides, herbicides, fungicides, and plant growth stimulants, and the like.

A wide variety of therapeutically active agents can be used in conjunction with the present invention. The therapeutically active agents (e.g. pharmaceutical agents) which may be used in the compositions of the present invention include both water soluble and water insoluble drugs. Examples of such therapeutically active agents include antihistamines (e.g., dimenhydrinate, diphenhydramine, chlorpheniramine and dexchlorpheniramine maleate), analgesics (e.g., aspirin, codeine, morphine, dihydromorphone, oxycodone, etc.), non-steroidal anti-inflammatory agents (e.g., naproxyn, diclofenac, indomethacin, ibuprofen, sulindac), anti-emetics (e.g., metoclopramide), anti-epileptics (e.g., phenytoin, meprobamate and nitrezepam), vasodilators (e.g., nifedipine, papaverine, diltiazem and nicardirine), anti-tussive agents and expectorants (e.g., codeine phosphate), anti-asthmatics (e.g. theophylline), antacids, anti-spasmodics (e.g. atropine, scopolamine), antidiabetics (e.g., insulin), diuretics (e.g., ethacrynic acid, bendrofluazide), antihypotensives (e.g., propranolol, clonidine), antihypertensives (e.g, clonidine, methyldopa), bronchodilators (e.g., albuterol), steroids (e.g., hydrocortisone, triamcinolone, prednisone), antibiotics (e.g., tetracycline), antihemorrhoidals, hypnotics, psychotropics, antidiarrheals, mucolytics, sedatives, decongestants, laxatives, vitamins, stimulants (including appetite suppressants such as phenylpropanolamine), as well as salts, hydrates, and solvates of the same. The above list is not meant to be exclusive.

In certain preferred embodiments, the therapeutically active agent comprises hydromorphone, oxycodone, dihydrocodeine, codeine, dihydromorphine, morphine, buprenorphine, salts, hydrates and solvates of any of the foregoing, mixtures of any of the foregoing, and the like.

In another preferred embodiment of the present invention, the active agent is a locally active therapeutic agent and the environment of use may be, e.g., the gastrointestinal tract, or body cavities such as the oral cavity, periodontal pockets, surgical wounds, the rectum or vagina.

The locally active pharmaceutical agent(s) include antifungal agents (e.g., amphotericin B, clotrimazole, nystatin, ketoconazole, miconazol, etc.), antibiotic agents (penicillins, cephalosporins, erythromycin, tetracycline, aminoglycosides, etc.), antiviral agents (e.g, acyclovir, idoxuridine, etc.), breath fresheners (e.g. chlorophyll), antitussive agents (e.g., dextromethorphan hydrochloride), anti-cariogenic compounds (e.g. metallic salts of fluoride, sodium monofluorophosphate, stannous fluoride, amine fluorides), analgesic agents (e.g., methylsalicylate, salicylic acid, etc.), local anesthetics (e.g., benzocaine), oral antiseptics (e.g., chlorhexidine and salts thereof, hexylresorcinol, dequalinium chloride, cetylpyridinium chloride), anti-flammatory agents (e.g., dexamethasone, betamethasone, prednisone, prednisolone, triamcinolone, hydrocortisone, etc.), hormonal agents (oestriol), antiplaque agents (e.g, chlorhexidine and silts thereof, octenidine, and mixtures of thymol, menthol, methysalicylate, eucalyptol), acidity reducing agents (e.g., buffering agents such as potassium phosphate dibasic, calcium carbonate, sodium bicarbonate, sodium and potassium hydroxide, etc.), and tooth desensitizers (e.g., potassium nitrate). This list is not meant to be exclusive.

In another preferred embodiment of the present invention, the active agent is disinfecting agent, e.g. a chlorine compound such as calcium hypochlorite, and the environment of use is a surrounding body of water, e.g. a recreational pool.

In still another preferred embodiment of the present invention, the active agent comprises at least one of a cleansing agent, a germicide, a deodorant, a surfactant, a fragrance, a perfume, a sanitizer, and/or a dye, and the environment of use is an aqueous solution, e.g. a urinal or toilet bowl.

In yet another preferred embodiment of the present invention, the active agent is a chemical impregnant, e.g. fertilizer, animal repellents, insect repellents, pesticides, herbicides, fungicides, plant growth stimulants, and the environment of use is, e.g., anywhere around the home, e.g. soil, trees etc. The fertilizer may be, for example, a nitrogen containing compound such as urea, urea formaldehyde composites, potassium nitrate, potassium sulfate, potassium chloride, ammonium nitrate, ammonium sulfate, monoammonium phosphate, dibasic ammonium phosphate, ammoniated super-phosphoric acid, micronutrient ingredients such as trace elements of iron, zinc, manganese, copper, boron, molybdenum, and mixtures of any of the foregoing. The fertilizer may be, e.g., in granular form. In these embodiments, the thickness of the controlled release coating will depend upon, among other things, the desired rate and overall time period for release of an effective amount of the active agent. In some circumstances where a relatively long time period of efficacy is desired, the substrate may be coated to a relatively high weight gain of, e.g., up to 50% or more. In other situations, it may be desirable to obtain the desired efficacy by utilizing coated substrates which are coated to different weight gains, or which include different components of the coating, so that a desired proportion of the coated substrates provide a release of active agent which is faster relative to other of the coated substrates, thereby providing an overall release of active agent which is within the desired effective levels for an even longer extended period of time.

For example, when the coated substrate is a coated chlorine tablet for combatting bacterial and algaecidal contamination of swimming pools and the like, the substrate may comprise commercial grade calcium hypochlorite, with or without trichloroisocyanuric acid, sodium dichlorocyanurate, lithium hypochlorite, powdered lime, and/or the like.

For example, the substrate may comprise about 98.5% commercial grade calcium hypochlorite and about 1.5% powdered lime, by weight. The substrate may also comprise commercial granular calcium hypochlorite, up to 20% by weight chloride of lime, and 1% zinc stearate having an available chlorine percentage of about 69% and a mass of about 57 g and a diameter of about 40 mm, as described in U.S. Pat. No. 4,192,763, hereby incorporated by reference. The substrate is then coated with the aqueous dispersion of plasticized hydrophobic polymer to a desired weight gain, and the coated tablet is then cured in accordance with the present invention until an endpoint is reached at which the cured coated tablet provides a reproducibly stable dissolution profile.

When the active agent comprises a composition suitable for cleaning and preventing the staining of toilet bowls, the substrate may include a well-known disinfectant such as calcium hypochlorite and/or trichloroisocyanuric acid. The active agent may alternatively comprise an alkali metal salt of dichloroisocyanuric acid and a chloride salt such as calcium chloride and barium chloride, such as that which is described in U.S. Pat. No. 4,654,341, hereby incorporated by reference.

One possible example of such a product might include a substrate comprising 0.5–5% fragrance, 1–10% dye, 10–40% surfactant (which may be nonionic, cationic, anionic or zwitterion surfactants), and other optional components such as germicides, disinfectants, processing aids, and other commonly included ingredients known to those skilled in the art. Such active agents may be incorporated into a substrate comprising a tablet, along with other well-known ingredients such as detergents, surfactants, perfumes, dyes, and any necessary fillers.

The substrate may be alternatively comprised of a pellet which is prepared by homogenously mixing together, e.g., 1 g of azure blue dye 65% (dye commercially available from Hilton David), 1 g Pluronic F-127 (a nonionic surfactant comprising the condensation products of ethylene oxide with the product resulting from the reaction of propylene oxide and ethylene diamine; commercially available from BASF-Wyandote Chemicals), 38 g Carbowax 8000 (a solid polyethylene glycol, molecular weight 8000; commercially available from Union Carbide), and 40 g Kemamide U (a oleylamide surfactant; commercially available from Witco) and an optional fragrance (e.g., 0.5% by weight citrus pine fragrance), and thereafter processing the above ingredients into a pellet by conventional methods such as noodling, plodding, extruding and cutting and stamping the mass to form the pellets. Optionally, the pellets may also include a suitable amount of an inorganic salt to cause the pellet to settle to the tank bottom, and one or more binding agents such as guar gum. The pellet is then coated with the aqueous dispersion of plasticized hydrophobic polymer to a weight gain from about 2 to about 30 percent, depending upon the desired rate of dissolution, and the coated pellet is then cured in accordance with the present invention until an endpoint is reached at which the cured coated pellet provides a reproducibly stable dissolution profile.

Another example of a substrate useful for the treatment of the flush water of toilets is one which comprises an iodophor such as povidone iodine, as described in U.S. Pat. No. 5,043,090, hereby incorporated by reference.

When the substrate comprises a fragrance, the fragrance may be any conventional commercially available perfume oil, e.g., volatile compounds including esters, ethers aldehydes, alcohols, unsaturated hydrocarbons, terpenes, and other ingredients which are well known in the art. Their type and compatibility is limited only by their compatibility and desirability, as may be determinable by those skilled in the art.

When the active agent comprises a composition suitable for use as a fertilizer, the active agent may comprise granular urea which is coated with the aqueous dispersion of plasticized hydrophobic polymer to a weight gain from about 2 to about 30 percent and then cured in accordance with the present invention. In urea pill production, urea at 70% solids concentration in water is heated to remove substantially all of the water. The molten urea is then injected as droplets to an air cooling tower where crystalline urea is formed as a hard pill or bead, which is then coated and cured in accordance with the present invention.

When the substrate comprises plant food formulations, the substrate can be pelleted, ball-shaped, particulate, or in stick form, and may additionally contain growth promoting substances such as gibberellic acid along with soil fungistats such as formaldehyde and paraformaldehyde, etc.

A split-screen Scanning Electron Micrograph (SEM) of a theophylline bead coated with an aqueous dispersion of Eudragit in accordance with the present invention prior to curing shows the distinct particles of acrylic polymers on the coating. Due to, e.g. cracks or pores in the coating, the environmental fluid can pass through to the underlying core where the active agent is found.

A split-screen SEM of the same theophylline bead taken after the bead has been cured in an oven at 45° C. for a time period of 48 hours shows apparent morphological changes to the coating on the surface of the bead.

When the controlled release coating of the present invention is to be applied to tablets, the tablet core (e.g. the substrate) may comprise the active agent along with any pharmaceutically accepted inert pharmaceutical filler (diluent) material, including but not limited to sucrose, dextrose, lactose, microcrystalline cellulose, xylitol, fructose, sorbitol, mixtures thereof and the like. Also, an effective amount of any generally accepted pharmaceutical lubricant, including the calcium or magnesium soaps may be added to the above-mentioned ingredients of the excipient prior to compression of the tablet core ingredients. Most preferred is magnesium stearate in an amount of about 0.2–5% by weight of the solid dosage form.

Tablets overcoated with a sufficient amount of the coating of acrylic resin to achieve a controlled release formulation pursuant to the present may be prepared and cured in similar fashion as explained above with regard to the preparation of beads. One skilled in the art will recognize that necessary curing conditions with regard to the particular elevated temperature, elevated humidity and time ranges necessary to obtain a stabilized product, will depend upon the particular formulation.

DETAILED DESCRIPTION OF THE PREFERRED EMBODIMENTS

The following examples illustrate various aspects of the present invention. They are not to be construed to limit the claims in any manner whatsoever.

EXAMPLE 1

Preparation of Hydromorphone Beads

Hydromorphone beads were prepared by dissolving hydromorphone HCl in water, adding Opadry® Y-5–1442, light pink (a product commercially available from Coloron, West Point, Pennsylvania, which contains hydroxypropyl methylcellulose (HPMC), hydroxypropyl cellulose, titanium dioxide, polyethylene glycol and D&C Red No. 30 Aluminum Lake), 20% w/w, and mixing for about 1 hour, and then spraying onto nu pariel 18/20 mesh beads using a Wurster insert. The resultant preparation had the formula set forth in Table 1 below:

TABLE 1

| Ingredients | Percent (by wt) | Amt/Unit (mg) |
|---|---|---|
| Hydromorphone HCl | 5.0% | 4.0 mg |
| Nu Pariel 18/20 | 92.5% | 74.0 mg |
| Opadry ® Lt. Pink Y-5-1442 | 2.5% | 2.0 mg |
| | 100.0% | 80.0 mg |

EXAMPLE 2

Retardant Coating—No Curing Step

In Example 2, hydromorphone beads prepared in accordance with Example 1 were overcoated with Eudragit® RS 30D to a 5% weight gain as set forth in Table 2 below. No terminal drying was conducted.

TABLE 2

| Ingredients | Percent (by wt) | Amt/Unit (mg) |
|---|---|---|
| Hydromorphone beads | 92.59 | 80 |
| Eudragit ® RS30D | 4.63 | 4 |
| Citroflex 2 (triethyl citrate) | 0.93 | 0.8 |
| Talc | 1.85 | 1.6 |
| Purified water | | qs |
| | 100 | 86.4 |

The hydromorphone beads were tested for initial dissolution, and then stored for one month under accelerated conditions of 37° C./80%RH (RH=relative humidity). After one month, the beads were found to have agglomerated.

Dissolution tests were carried out via the USP Basket Method, 37° C., 100 RPM, first hour 700 ml gastric fluid at pH 1.2, then changed to 900 ml at 7.5. The dissolution was conducted by placing an open capsule containing an appropriate weight of beads into a vessel. The results are set forth in Table 3 below:

TABLE 3

Hydromorphone HCl 12 mg Controlled Released Capsules
Stability Performance Data

| Time | Hydromorphone HCl | Average Fill Wt (mg) | 1 hr | 2 hr | 4 hr | 8 hr | 12 hr | 18 hr | 24 hr |
|---|---|---|---|---|---|---|---|---|---|
| Initial | 12.34 | 259.2 | 1.5 | 5.1 | 15.6 | 53.5 | 76.9 | 93.6 | 100.0 |
| 37° C./80% RH | | | | | | | | | |
| 1 mo. | 12.42 | 262.6 | 2.1 | 6.1 | 12.6 | 35.1 | 56.2 | 75.1 | 86.1 |

The above results demonstrate that there was a slowing of the dissolution of hydromorphone HCl from the coated beads when the beads were subjected to accelerated storage conditions.

EXAMPLE 3

Protecting the Retardant Coating

In order to determine if the slowing of the dissolution of the hydromorphone beads of Example 2 was due to a stability problem between the hydromorphone and the retardant, in Example 3 Nu pariel hydromorphone beads were prepared according to Example 1, then overcoated with 5% HPMC, and tested without the retardant layer. Dissolution tests were conducted initially, and after storage at accelerated conditions of 37° C. dry and 37° C./80%RH.

The results of the dissolution tests for Example 3 are set forth in Table 4 below:

TABLE 4

Hydromorphone HCl 8 mg Controlled Release Capsules
Stability Data Summary

| Testing Time | Hydromorphone HCl | Average Weight (mg) | 1 hr | 2 hr |
|---|---|---|---|---|
| Initial | 8.49 | 166 | 100.0 | 100.0 |
| 37° C. dry | | | | |
| 1 month | 8.49 | 167 | 100.0 | 100.0 |
| 2 months | 8.49 | 167 | 100.0 | 100.0 |
| 37° C./80% RH | | | | |
| 1 month | 8.49 | 167 | 100.0 | 100.0 |
| 2 months | 8.49 | 170.3 | 100.0 | 100.0 |

The results of Example 3 show that the coated beads which did not include a retardant coating were stable.

In order to determine the relative humidity under "dry conditions" in the oven, the relative humidity in a water-filled desiccator in a 60° C. oven was determined as follows. First, about 500 grams of purified water is poured into a plastic desiccator and the metal guard inserted. A hygrometer/temperature indicator is placed on top of the guard and the desiccator covered and placed in the 60° C. oven for 24 hours. After 24 hours the relative humidity in the desiccator was 85% while the temperature was still 60° C. On placing the hygrometer alone in the 60° C. oven for 24 hours, the relative humidity was 9% at 60° C.

EXAMPLE 4

Prior Art Curing (According to Literature Recommendations)

In Example 4, hydromorphone beads prepared according to Example 3 were coated with the Eudragit® RS to a 5% weight gain. After application of the coating, the beads were dried (cured) at 45° C. in a fluidized bed dryer for 2 hours. This temperature is above the Tg of Eudragit® RS 30D, plasticized with Triethylcitrate at 20% level of solids. Dissolution tests were conducted initially, and after storage at 37° C. dry and 37° C./80%RH. The results are set forth in Table 5 below:

TABLE 5

Hydromorphone HCl 8 mg Controlled Release Capsules
Stability Data Summary

| Testing Time | Hydromorphone HCl | Average Weight (mg) | 1 hr | 2 hr | 4 hr | 8 hr | 12 hr | 18 hr |
|---|---|---|---|---|---|---|---|---|
| 2 hours* | 8.50 | 178.5 | 8.0 | 21.8 | 45.7 | 79.3 | 94.2 | |
| 37° C. dry | | | | | | | | |
| 1 mo. | 8.50 | 177 | 16.8 | 25.8 | 44.2 | 67.8 | 80.8 | |
| 2 mo. | 8.39 | 174 | 24.6 | 40.8 | 61.8 | 83.4 | 94.0 | 100.0 |

TABLE 5-continued

Hydromorphone HCl 8 mg Controlled Release Capsules
Stability Data Summary

| Testing Time | Hydromorphone HCl | Average Weight (mg) | 1 hr | 2 hr | 4 hr | 8 hr | 12 hr | 18 hr |
|---|---|---|---|---|---|---|---|---|
| 37° C./80% RH | | | | | | | | |
| 1 mo. | 8.50 | 174 | 48.8 | 60.1 | 80.7 | 94.0 | 100.0 | |
| 2 mo. | 8.55 | 178 | 53.6 | 76.3 | 90.7 | 98.2 | 100.0 | |

*initial dissolution after curing

From the results provided above, it can be seen that the hydromorphone dissolution from the beads underwent significant changes upon storage, and that the short curing step recommended in the literature and utilized in Example 4 did not to help the stability/curing problem.

EXAMPLES 5–7

Optimizing Curing and Ingredients of Retardant Coating

The results obtained from Examples 2–4 indicated that the dissolution of the beads overcoated with a retardant coating seemed to slow down to a point and no further. However, the endpoint dissolutions achieved were too slow.

In Examples 5–7, additional tests were conducted to determine processing conditions required during manufacture to cure the product to its endpoint dissolution.

In order to obtain a formulation having a more suitable dissolution curve, and, rather than reduce the coating to less than 5% weight gain, the more soluble Eudragit® RL (methacrylic ester 1:20 quaternary ammonium groups) was included in the retardant coat.

In Examples 5–7, the hydromorphone beads prepared pursuant to Example 4, except that they were overcoated with a 5% HPMC to protect the retardant coating from the environment. In Example 5, the retardant coating consisted of 100% Eudragit® RL. In Example 6, the retardant coating consisted of 50% Eudragit® RL and 50% Eudragit® RS. Finally, In Example 7, the retardant coating consisted of 10% Eudragit® RL: Eudragit® 90% RS. Each of Examples 5–7 were coated to total weight gain of 5%.

Each of the HPMC-protected coatings of Examples 5–7 were cured to 1, 2, 7, 10, 21 and 30 days at 45° C. dry, at which times dissolution studies as set forth in Example 2 were conducted.

Only Example 7 showed a desirable release profile, and curing was complete after only one day. Dissolution studies of the products of Examples 5 and 6 showed the same to be immediate release products, the amount/type of retardant used not being sufficient to prevent immediate release of the drug (i.e., about 100% of the drug being released after one hour), even after the formulations were cured. Example 7 was further tested by storing under accelerated conditions as follows. After curing for 21 days, the samples of Example 7 were placed in a 37° C./80%RH oven, and dissolution tests as set forth in Example 2 were conducted after 7 and 30 days. Representative dissolution profiles for Example 7 (mean results for three samples) are set forth in Table 6 below:

TABLE 6

Hydromorphone HCl 8 mg MD CR Eudragit® 5% Beads

| Curing Time | Wt(mg) | Percent Hydromorphone HCl Dissolved | | | | | | |
|---|---|---|---|---|---|---|---|---|
| | | 1 hr | 2 hr | 4 hr | 8 hr | 12 hr | 18 hr | 24 hr |
| Initial | | | | | | | | |
| Mean 1 day | 191 | 16.6 | 53.1 | 69.3 | 86.7 | 95.6 | 99.3 | 100.0 |
| Mean 2 days | 190.7 | 7.1 | 33.1 | 66.6 | 87.3 | 99.5 | 97.9 | 99.0 |
| Mean 7 days | 190.7 | 7.4 | 35.0 | 67.0 | 87.4 | 95.1 | 98.4 | 99.2 |
| Mean 10 days | 190.7 | 8.0 | 36.3 | 67.7 | 86.6 | 93.3 | 96.8 | 98.4 |
| Mean 21 days | 191.3 | 7.2 | 36.5 | 68.9 | 88.5 | 94.8 | 98.0 | 99.5 |
| Mean 30 days | 191 | 6.9 | 36.1 | 66.9 | 86.2 | 92.7 | 99.8 | 99.0 |
| Mean Storage Time/ Conditions 30° C./ 80% RH 7 days | 190.3 | 5.83 | 31.9 | 65.2 | 82.7 | 90.4 | 96.3 | 96.7 |
| Mean 30 days | 190.7 | 5.9 | 25.1 | 62.7 | 84.6 | 92.6 | 97.6 | 99.5 |
| Mean | 190.3 | 5.8 | 31.9 | 65.2 | 82.7 | 90.4 | 96.3 | 96.9 |

The results set forth in Table 6 demonstrate that the 1 month dissolution profile showed no slowdown as compared to the initial cured sample, even for the samples tested under accelerated conditions. Thus, after curing for 24 hours at 45° C., the methacrylate controlled release film coating was essentially stabilized.

EXAMPLES 8–10

Optimizing Retardant Coating Thickness

In Examples 8–10, additional experimentation was conducted to determine the optimum weight of methacrylate polymer to use for a desirable release profile and to determine reproducibility and effectiveness of the 48 hour curing step at 45° C. dry. Three batches were manufactured at different levels of methacrylate load and cured in a 45° C. dry oven.

In Example 8, hydromorphone beads were prepared in accordance with those of Example 3, as set forth in Table 7 below:

TABLE 7

Hydromorphone HCl MD Beads

| Ingredients | Percent (by wt) | Amt/Unit (mg) |
|---|---|---|
| Hydromorphone HCl | 4.75% | 4 |
| Nupariels Pa 18/20 | 87.89% | 74 |
| Opadry Lt Pink Y-5-1442 | 2.38% | 2 |
| Opadry Lt Pink Y-5-1442 | 4.99% | 4.2 |
|  | 100% | 84.2 |

The hydromorphone beads were then further processed in accordance with Example 5. In Example 7, the retardant coating was Eudragit® RS, Eudragit® RL 90:10 (5% w/w coating). The formula for Example 7 is set forth in Table 8 below:

TABLE 8

Hydromorphone HCl MD CR Eudragit ® 5% Beads

| Ingredients | Percent (by wt) | Amt/Unit (mg) |
|---|---|---|
| Hydromorphone beads | 87.96% | 84.2 mg |
| Eudragit ® RS 30D (90%) | 3.97% | 3.8 mg |
| Eudragit ® RL 30D (10%) | 0.42% | 0.4 mg |
| TEC (20% of RS & RL) | 0.88% | 0.84 mg |
| Talc (40% of RS & RL) | 1.75% | 1.68 mg |
| Purified water |  | qs |
| Opadry Lt Pink Y-5-1442 | 5.01% | 4.8 |
|  | 100% | 95.72 mg |

Examples 9 and 10 are prepared in similar fashion to Example 7. In Example 9, the retardant coating was Eudragit® RS, Eudragit® RL 90:10 (8% w/w coating). In Example 10, the retardant coating was Eudragit® RS, Eudragit® RL 90:10 (12% w/w coating). The formulas for Examples 9 and 10 are set forth in Tables 9 and 10, respectively, below:

TABLE 9

Hydromorphone HCl MD CR Eudragit ® 8% Spheres

| Ingredients | Percent (by wt) | Amt/Unit (mg) |
|---|---|---|
| Hydromorphone beads | 84.2% | 84.2 |
| Eudragit ® RS 30D (90%) | 6.07% | 6.07 |
| Eudragit ® RL 30D (10%) | 0.67% | 0.67 |
| TEC (20% of RS & RL) | 1.35% | 1.35 |
| Talc (40% of RS & RL) | 2.70% | 2.70 |
| Purified water |  | qs |
| Opadry Lt Pink Y-5-1442 | 5.0% | 5.0 |
|  | 99.99% | 99.99 |

TABLE 10

Hydromorphone HCl MD CR Eudragit ® 12% Spheres

| Ingredients | Percent (by wt) | Amt/Unit (mg) |
|---|---|---|
| Hydromorphone beads | 79.69% | 84.2 |
| Eudragit ® RS 30D (90%) | 8.61% | 9.1 |
| Eudragit ® RL 30D (10%) | 0.95% | 1.0 |
| TEC (20% of RS & RL) | 1.91% | 2.02 |

TABLE 10-continued

Hydromorphone HCl MD CR Eudragit ® 12% Spheres

| Ingredients | Percent (by wt) | Amt/Unit (mg) |
|---|---|---|
| Talc (40% of RS & RL) | 3.82% | 4.04 |
| Purified water |  | qs |
| Opadry Lt Pink Y-5-1442 | 5.02% | 5.3 |
|  | 100% | 105.66 |

Each of Examples 9–10 were cured on paper lined trays in a 45° C. oven for two days after the application of the Eudragit® Controlled Release coating and the HPMC 5% overcoating. Dissolution studies were then conducted on Examples 8–10.

Initial dissolution profiles (after curing) of Example 8 showed it to resemble Example 7 (the products of both Examples were overcoated with a 5% w/w Eudragit® coating). After curing for 2 days, samples of Example 8 were subjected to further tests at room temperature, and under accelerated conditions of 37° C./80%RH, 37° C. dry and 50° C. dry. Representative dissolution profiles for Example 8 (mean results for three samples) are set forth in Table 11 below:

TABLE 11

Hydromorphone HCl CR 8 mg Eudragit ® 5% Capsules

| | | Percent Hydromorphone HCl Dissolved | | | | | | |
|---|---|---|---|---|---|---|---|---|
| Time | Wt(mg) | 1 hr | 2 hr | 4 hr | 8 hr | 12 hr | 18 hr | 24 hr |
| 2 days* | | | | | | | | |
| Mean RT 1 mo. | 191.3 | 6.3 | 36.2 | 69.3 | 87.8 | 97.3 | 100.0 | |
| Mean 37° C./ 80% RH 1 mo. | 191.1 | 6.0 | 30.8 | 63.1 | 83.4 | 91.8 | 96.3 | 97.9 |
| Mean 2 mo. | 191.6 | 6.9 | 28.5 | 63.2 | 84.5 | 91.5 | 95.6 | 97.8 |
| Mean 37° C. Dry 1 mo. | 194.3 | 11.4 | 35.6 | 70.7 | 90.5 | 96.8 | 100 | |
| Mean 50° C. Dry 1 mo. | 192.0 | 11.4 | 35.1 | 68.6 | 87.9 | 94.5 | 98.9 | 100 |
| Mean | 191.4 | 11.1 | 41.4 | 70.6 | 90.4 | 96.5 | 100 | |
| Comparison to Example 9 (1 day and 2 day dissolutions) | | | | | | | | |
| 1 day | | | | | | | | |
| Mean 2 Days | 190.7 | 7.1 | 33.1 | 66.6 | 87.3 | 99.5 | 97.9 | 99.0 |
| Mean | 190.7 | 7.4 | 35.0 | 67.0 | 87.4 | 95.1 | 98.4 | 99.2 |

*initial dissolution after curing

As can be seen from the dissolution results provided for Example 8, although the dissolution profile of the samples were not taken after 1 day of curing, the results obtained after 2 day curing are substantially similar to the results obtained for the 1 and 2 day curings of Example 7. Therefore, it is hypothesized that the product of Example 8 was also stable after one day curing.

After curing for 2 days, samples of Example 9 were tested for dissolution, and then samples of Example 9 were exposed to accelerated conditions of 37° C./80%RH for one month. Representative initial dissolution profiles (mean results for three samples) for Example 9 are set forth in Table 12 below:

TABLE 12

Hydromorphone HCl CR 8 mg Eudragit ® 8% Capsules

| | | Percent Hydromorphone HCl Dissolved | | | | | | |
|---|---|---|---|---|---|---|---|---|
| Time | Wt(mg) | 1 hr | 2 hr | 4 hr | 8 hr | 12 hr | 18 hr | 24 hr |
| 2 days* | | | | | | | | |
| Mean | 201.3 | 0.8 | 3.3 | 40.0 | 78.4 | 90.7 | 97.5 | 99.9 |
| 37° C./80% RH 1 mo. | | | | | | | | |
| Mean | | 7.3 | 8.6 | 34.1 | 72.8 | 85.5 | 93.2 | 97.2 |

*initial dissolution after curing

As can be seen from the dissolution results provided above for Example 9, the results obtained after 2 day curing are substantially similar to the results obtained under accelerated storage conditions of 37° C./80%RH, thus indicating the stability of Example 9 after a 2 day curing. Furthermore, the dissolution results obtained with Example 9 showed slower release rates of hydromorphone, as would be expected given the thicker retardant coating.

After curing for 2 days, samples of Example 10 were tested for dissolution, and then samples of Example 10 were subjected to further tests after storing for one month at room temperature, and under accelerated conditions of 37° C./80%RH, 37° C. dry and 50° C. dry. Representative dissolution profiles (mean results for three samples) for Example 10 are set forth in Table 13 below:

TABLE 13

Hydromorphone HCl CR 8 mg Eudragit ® 12% Capsules

| | | Percent Hydromorphone HCl Dissolved | | | | | | |
|---|---|---|---|---|---|---|---|---|
| Time | Wt(mg) | 1 hr | 2 hr | 4 hr | 8 hr | 12 hr | 18 hr | 24 hr |
| 2 days* | | | | | | | | |
| Mean RT 1 mo. | 215.3 | 0.8 | 3.1 | 9.3 | 70.9 | 90.4 | 100.8 | 104.8 |
| Mean 37° C./ 80% RH 1 mo.- | 210.8 | 0 | 1.8 | 4.6 | 62.9 | 84.3 | 96.1 | 99.8 |
| Mean 37° C. Dry 1 mo. | 213.8 | 2.2 | 4.8 | 7.2 | 50.8 | 74.3 | 87.3 | 93.3 |
| Mean 50° C. Dry 1 mo. | 210.4 | 0.8 | 2.2 | 6.9 | 59.7 | 82.2 | 96.3 | 100 |
| Mean | 207.3 | 1.6 | 1.5 | 3.3 | 51.5 | 76.2 | 90.9 | 97.4 |

*initial dissolution after curing

As can be seen from the dissolution results provided above for Example 10, the dissolution results obtained with Example 10 showed slower release rates of hydromorphone as compared to the thinner retardant coatings of Examples 8 and 9, as expected. The overall results obtained after 2 day curing are substantially similar to the results obtained under accelerated storage conditions of 37° C./80%RH, with the exception of the percent drug dissolved at the 8 hour and 12 hour points. These results might indicate that at high loads of retardant coating, it may be necessary to cure the coating for a longer period of time to attain a stabilized formulation.

EXAMPLE 11

Morphine Sulfate Coated Beads

In Example 11, the curing step of the present invention was applied to a formulation in which morphine sulfate was substituted as the drug.

A suspension of morphine sulfate and HPMC (Opadry® Clear Y-5-7095) was applied onto 18/20 mesh nupariel beads in a fluid bed dryer with a Wurster insert at an inlet temperature of 60° C. An Opadry® Lavender YS-1-4729 HPMC Base filmcoating suspension was then applied after drug loading as a protective coat at a 5% weight gain.

After the overcoating process was completed, the morphine sulfate beads were then overcoated with a retardant coating mixture of Eudragit® RS 30D and Eudragit® RL 30D at a ratio of 90:10, RS to RL, at a 5% weight gain level. The application of this mixture of Eudragit® RS 30D and Eudragit® RL 30D along with talc (included as an antitacking agent) and triethyl citrate (plasticizer) was done at an inlet temperature of 35° C. in a Wurster Insert.

Once the retardant overcoating was complete, the morphine sulfate beads were given a final overcoating of Opardry® lavender YS-1-4729 at a 5% weight gain level.

After completion of the final filmcoating process, the morphine sulfate beads were cured on paper lined trays in a 45° C. dry oven for 2 days. After curing, the beads were filled into gelatin capsules at a 30 mg morphine sulfate strength. The final formula is provided in Table 14 below:

TABLE 14

| Processing Step | Ingredient | Mg/Capsule |
|---|---|---|
| Drug Load | Morphine Sulfate | 30 mg |
| | Nupariel PG 18/20 | 255 mg |
| | Opadry ® Clear Y-5-7095 | 15 mg |
| First Overcoat | Opadry ® Lavender YS-1-4729 | 15.8 mg |
| Retardant Overcoat | Eudragit ® RS 30D | 14.2 mg |
| | Eudragit ® RL 30D | 1.6 mg |
| | Triethylcitrate | 3.2 mg |
| | Talc | 6.3 mg |
| Final overcoat | Opadry ® Lavender YS-1-4729 | 18.0 mg |
| | Total: | 359.1 mg |

Dissolution stability studies were then conducted on the product of Example 11 after the above-mentioned curing step at storage conditions of room temperature, 37° C./80%RH, 37° C. dry, and 50° C. dry after one month and after two months. The results are set forth in Table 15 below:

TABLE 15

Morphine Sulfate CR 30 mg Eudragit ® 5% Capsules

Percent Morphine Sulfate Dissolved

| Time | 1 hr | 2 hr | 4 hr | 6 hr | 8 hr | 12 hr | 18 hr | 24 hr |
|---|---|---|---|---|---|---|---|---|
| 2 days* | | | | | | | | |
| Mean RT 1 mo. | 0.0 | 43.5 | 74.9 | — | 91.8 | 95.3 | 99.8 | 100 |
| Mean 2 mo. | 0.0 | 36.9 | 73.8 | 86.9 | 92.2 | 96.5 | 99.9 | 100 |
| Mean 37° C./80% RH 1 mo. | 2.0 | 37 | 72 | 82 | 88 | 92 | 96 | 99 |
| Mean 2 mo. | 0.0 | 28.4 | 70.3 | 84.8 | 92.1 | 97.7 | 100 | |
| Mean 37° C. Dry 1 mo. | 1.9 | 30.1 | 68.4 | 79.9 | 87.0 | 93.5 | 95.6 | 97.8 |
| Mean 2 mo. | 0.0 | 32.0 | 72.5 | 86.0 | 93.2 | 97.3 | 100 | |
| Mean 50° C. Dry 1 mo. | 0.9 | 26.4 | 67.5 | 78.8 | 88.6 | 94.0 | 98.0 | 99.5 |
| Mean 2 mo. | 0.0 | 37.7 | 74.1 | 89.3 | 93.7 | 98.5 | 100 | |
| Mean | 2.0 | 33.0 | 74 | 85 | 94 | 98 | 100 | |

*initial dissolution after curing

The results set forth in Table 15 demonstrate that the curing process stabilized the dissolution profile of the morphine sulfate to an endpoint dissolution rate which substantially remained constant, even for the samples stored under accelerated conditions.

EXAMPLE 12

Controlled Release Hydromorphone HCl 8 Mg Formulations—Acrylic Polymer Coating

Example 12 is prepared as follows:

1. Drug Loading. Hydromorphone beads were prepared by dissolving hydromorphone HCl in water, adding Opadry Y-5-1442, light pink (a product commercially available from Colorcon, West Point, PA, which contains hydroxypropyl methylcellulose, hydroxypropyl cellulose, titanium dioxide, polyethylene glycol and D&C Red No. 30 aluminum lake) and mixing for about 1 hour to obtain a 20% w/w suspension. This suspension was then sprayed onto Nu-Pareil 18/20 mesh beads using a Wurster insert.

2. First Overcoat. The loaded hydromorphone beads were then overcoated with a 5% w/w gain of Opadry Light Pink using a Wurster insert. This overcoat was applied as a protective coating.

3. Retardant Coat. After the first overcoat, the hydromorphone beads were then coated with a 5% weight gain of a retardant coating mixture of Eudragit RS 30D and Eudragit RL 30D at a ratio of 90:10, RS to RL. The addition of Triethyl Citrate (a plasticizer) and Talc (anti-tacking agent) was also included in the Eudragit suspension. The Wurster insert was used to apply the coating suspension.

4. Second Overcoat. Once the retardant coating was complete, the hydromorphone beads were given a final overcoat of Opadry Light Pink to a 5% weight gain using a Wurster insert. This overcoat was also applied as a protective coating.

5. Curing. After the completion of the final overcoat, the hydromorphone beads were cured in a 45° C. oven for 2 days. The cured beads were then filled into gelatin capsules at an 8 mg Hydromorphone strength. The complete formula for the beads of Example 12 is set forth in Table 16 below:

TABLE 16

| Processing Step | Ingredient | % | mg/unit |
|---|---|---|---|
| Drug Loading | Hydromorphone HCl | 8.2 | 8.0 |
| | Nu-Pareil 18/20 | 73.3 | 74.0 |
| | Opadry Lt Pink | 2.1 | 2.0 |
| First Overcoat | Opadry Lt Pink | 4.4 | 4.2 |
| Retardant Coat | Eudragit RS 30D (dry wt.) | 4.0. | 3.8 |
| | Eudragit RL 30D (dry wt.) | 0.4 | 0.4 |
| | Triethyl Citrate | 0.8 | 0.8 |
| | Talc | 1.8 | 1.7 |
| Second Overcoat | Opadry Lt Pink | 5.0 | 4.8 |
| Total | | 100.0 | 99.7 mg |

Dissolution studies were conducted on the Eudragit-coated hydromorphone beads of Example 12 both initially and after 28 days. The results are set forth in Table 17 below:

TABLE 17

| Time | 1 hr | 2 hr | 4 hr | 8 hr | 12 hr | 18 hr | 24 hr |
|---|---|---|---|---|---|---|---|
| Initial | 17.2 | 48.4 | 77.4 | 93.3 | 97.2 | 98.8 | 98.8 |
| 28 days at 37° C./80% RH | 16.8 | 50.6 | 79.7 | 95.2 | 99.0 | 101.9 | 102.7 |

The stability studies of the Eudragit-coated hydromorphone beads as set forth in Table 17 below show the initial dissolution to be the same as the dissolution done on samples placed at a 37° C./80% RH condition.

EXAMPLE 13

In Example 13, a single dose six-way randomized crossover study (one week wash-out) was conducted in 12 patients and compared to the results obtained with an equivalent dose of an immediate release preparation. Blood samples were taken initially, 0.25, 0.5, 0.75, 1, 1.5, 2, 2.5, 3, 3.5, 4, 6, 8, 10, 12, 18, 24, 30, 36 and 48 hours after administration in order to determine plasma levels. Comparative Example 13A is 8 mg of a hydromorphone immediate release formulation (two tablets of Dilaudid® 4 mg tablets, commercially available from Knoll). Example 13 is an 8 mg dose of the encapsulated hydromorphone beads of Example 12.

Figure 2:
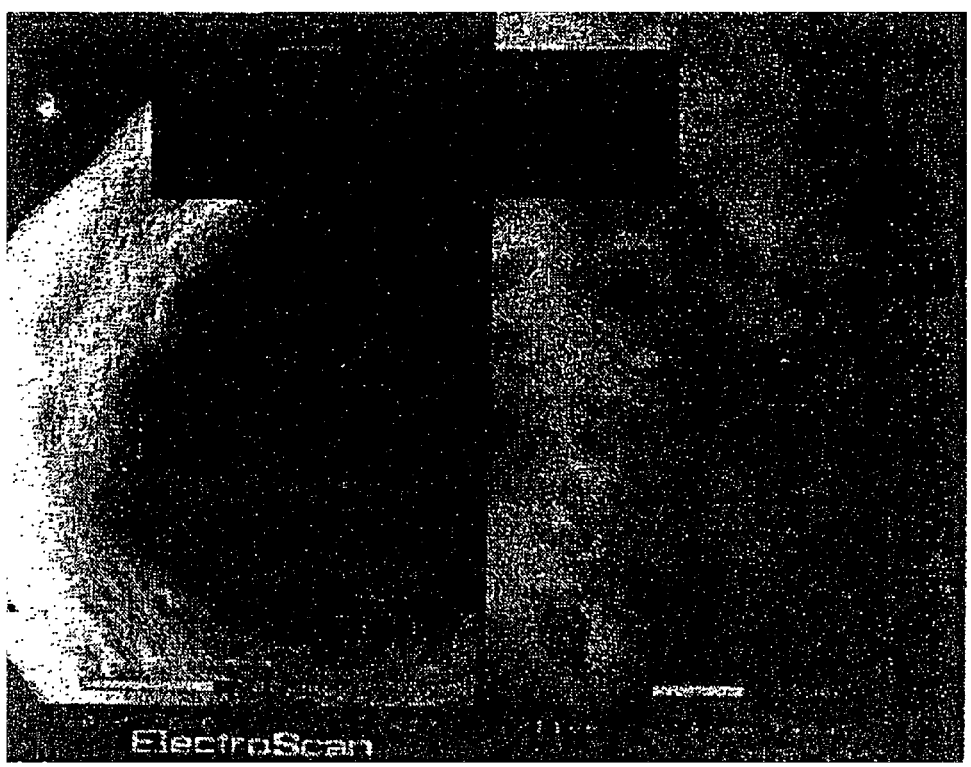
FIG. 2 is a graphical representation of the dissolution results of Example 5.
Figure 3:
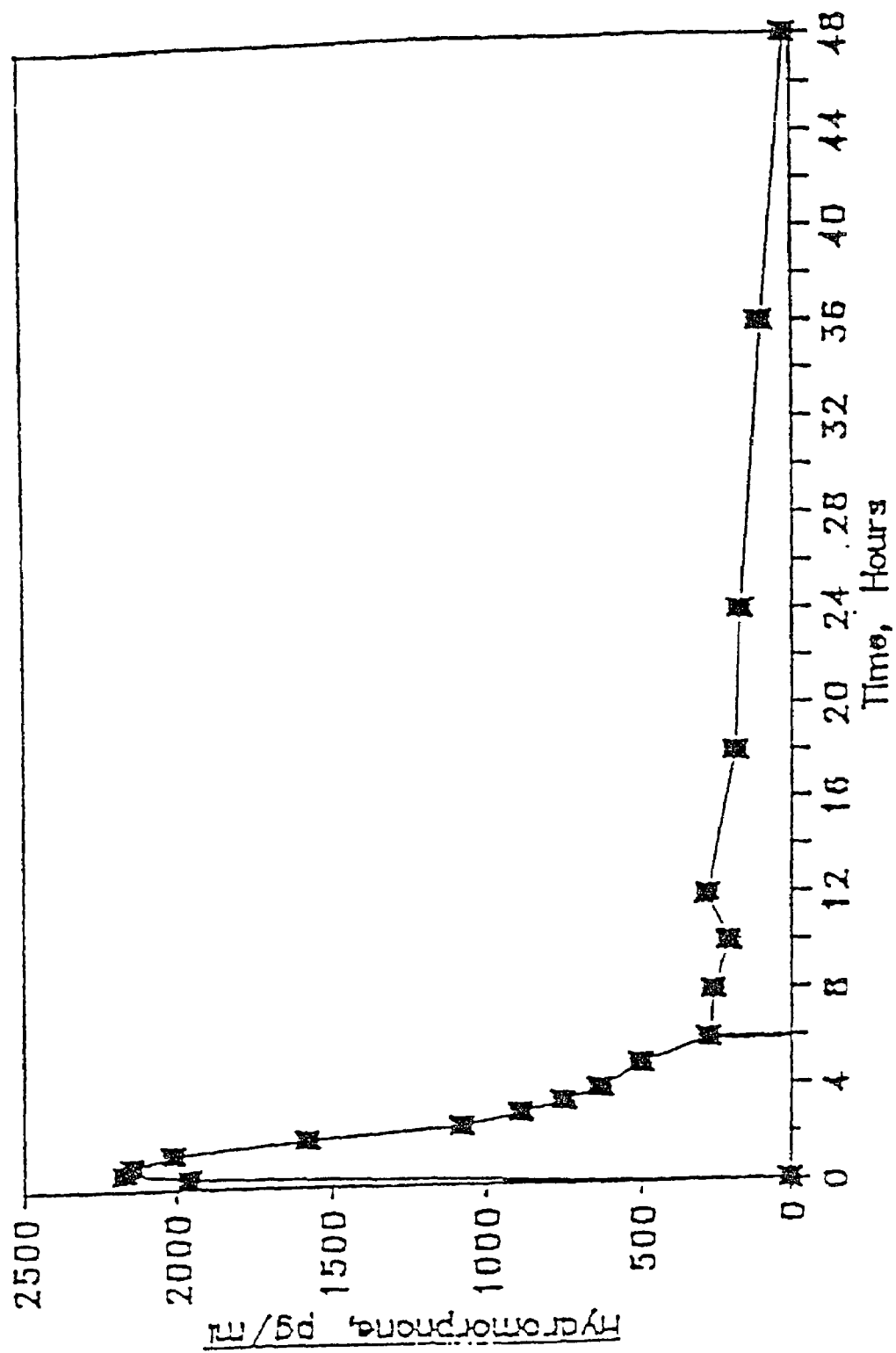
FIG. 3 is a graphical representation comparing the plasma levels obtained by Example 13 against the plasma levels obtained by Comparative Example 13A.

The results obtained for Comparative Example 13A are set forth in FIG. 1. The results obtained for Example 5 are set forth in FIG. 2. FIG. 3 shows the plasma levels of Example 13 plotted against the results for Comparative Example 13A. The results for Example 13 are further set forth in Table 18 below, which provides data regarding area under the curve (bioavailability), the peak plasma concentration ($C_{max}$), and the time to reach peak plasma concentration ($T_{max}$).

TABLE 18

| Product | AUC | Cmax | Tmax | PW@HH |
|---|---|---|---|---|
| Example 13A 2 Dilaudid 4 mg Tablets | 12427 ± 1792 | 3013 ± 539 | 1.10 ± 0.14 | 1.67 ± 0.22 |
| Example 13 | 13707 ± 1381 | 1211 ± 153 | 4.42 ± 0.38 | 7.79 ± 1.96 |
| Example 13 | 110% | 40% | 402% | 466% |

The results obtained for Example 13 showed that at the 12th hour after administration, the blood levels of hydromorphone are over 500 pg/ml hydromorphone, and at the 24th hour after administration, the plasma levels are well over 300 pg/ml. Therefore, this product is considered to be suitable for once a day administration.

EXAMPLES 14–15

In Examples 14–15, a single dose 4-way randomized crossover study was conducted in 10 subjects. Example 14 was an 8 mg dose of the hydromorphone beads of Example 13—fasted; whereas Example 15 is an 8 mg dose of the hydromorphone beads of Example 13—fed. In Comparative Example 14A, 8 mg of immediate release hydromorphone (2 Dilaudid 4 mg tablets) were administered—fasted. In Comparative Example 15A, 8 mg of immediate release hydromorphone (2 Dilaudid 4 mg tablets) were administered—fed.

Figure 4:
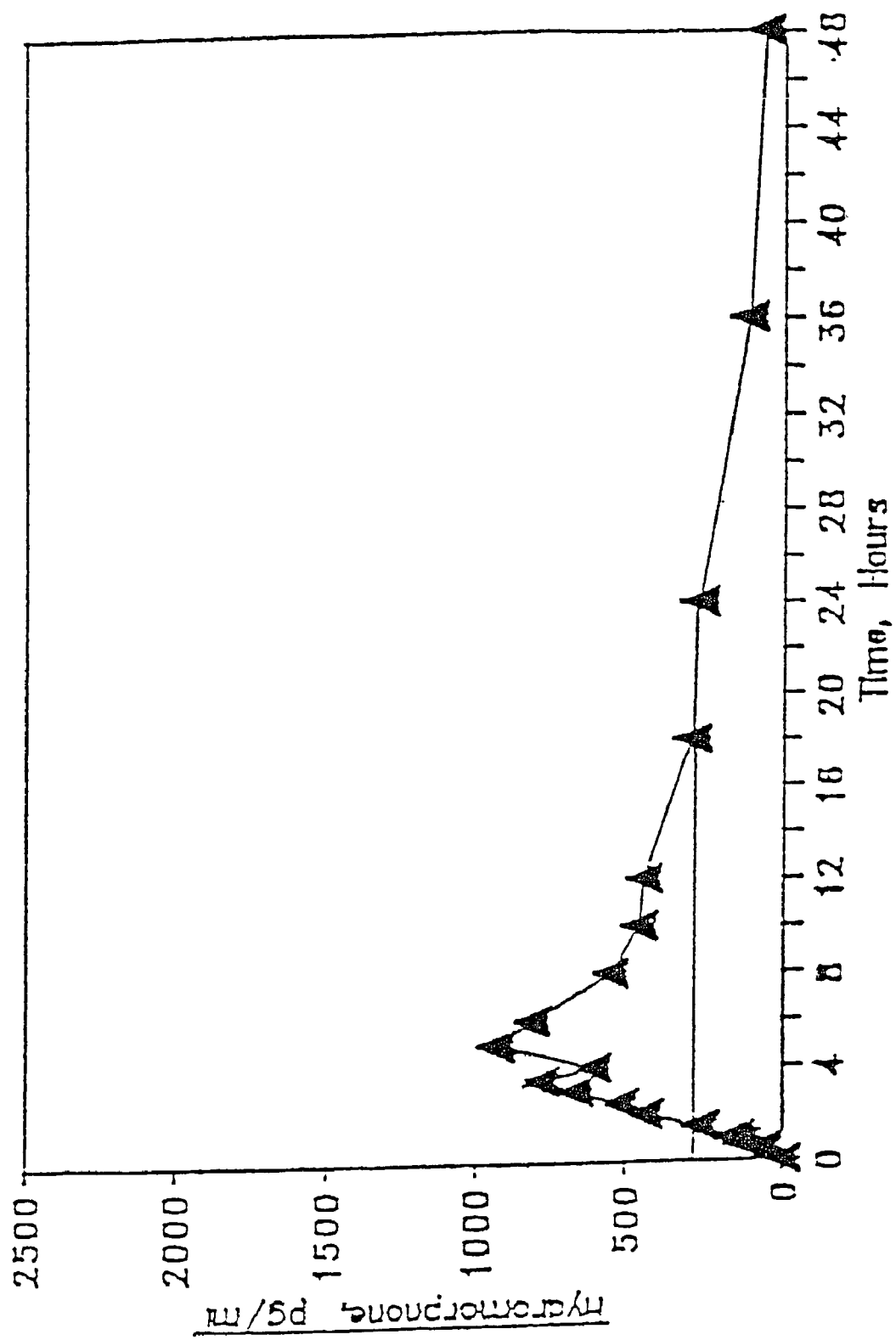
FIG. 4 is a graphical representation of the plasma levels obtained for Examples 14A and 15A.
Figure 5:
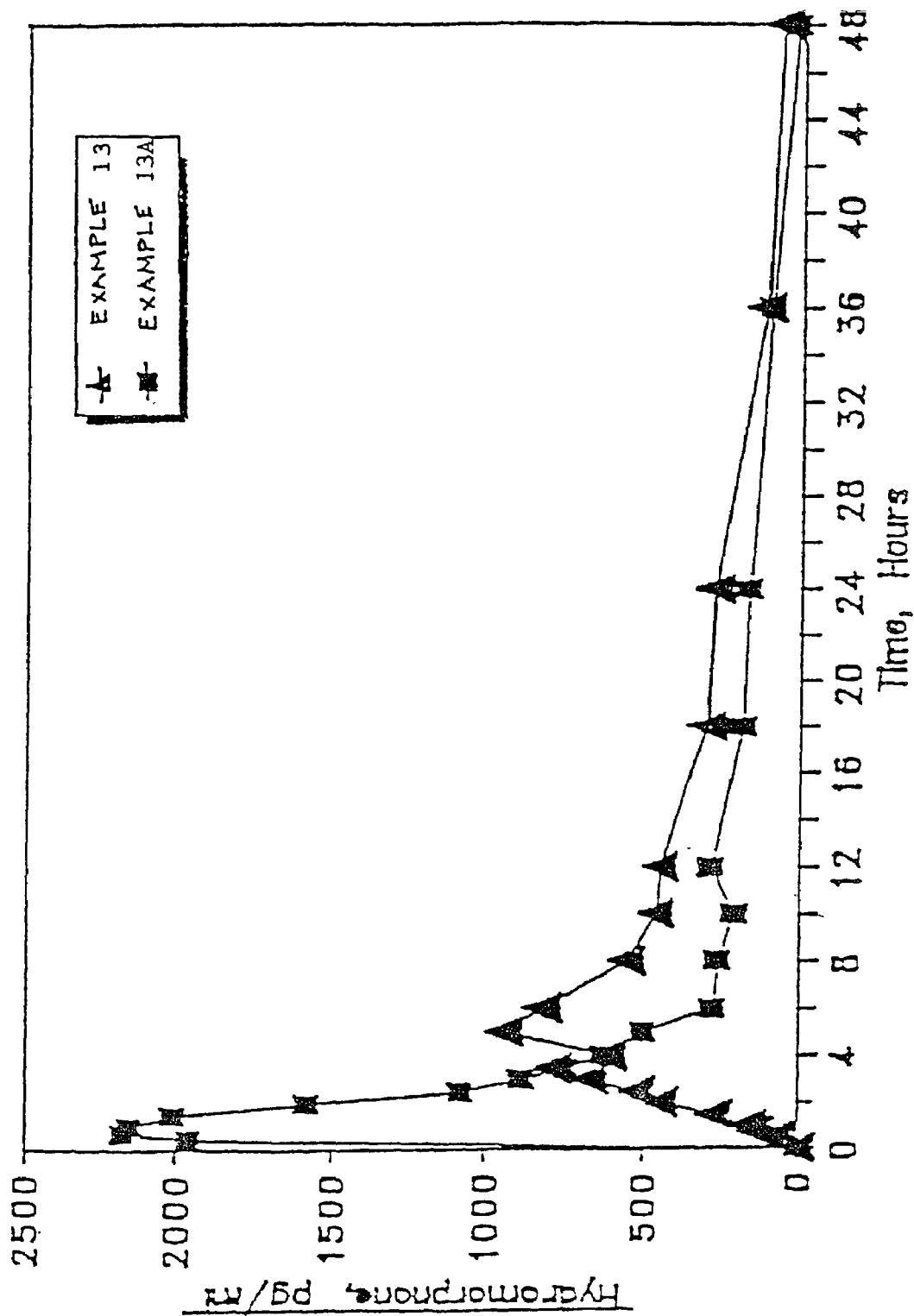
FIG. 5 is a graphical representation of the plasma levels obtained for Examples 14 and 15.
Figure 6:
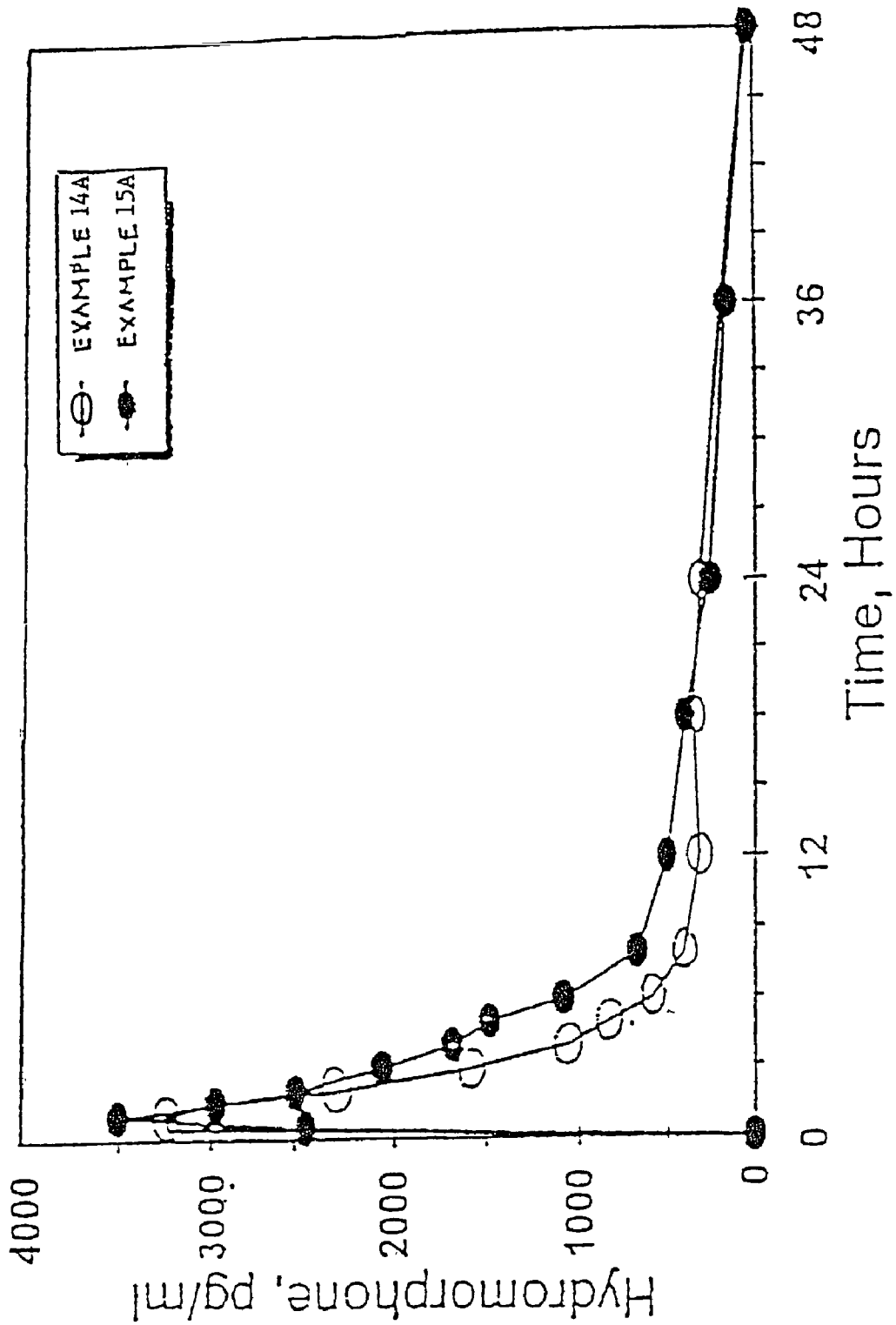
Figure 7:
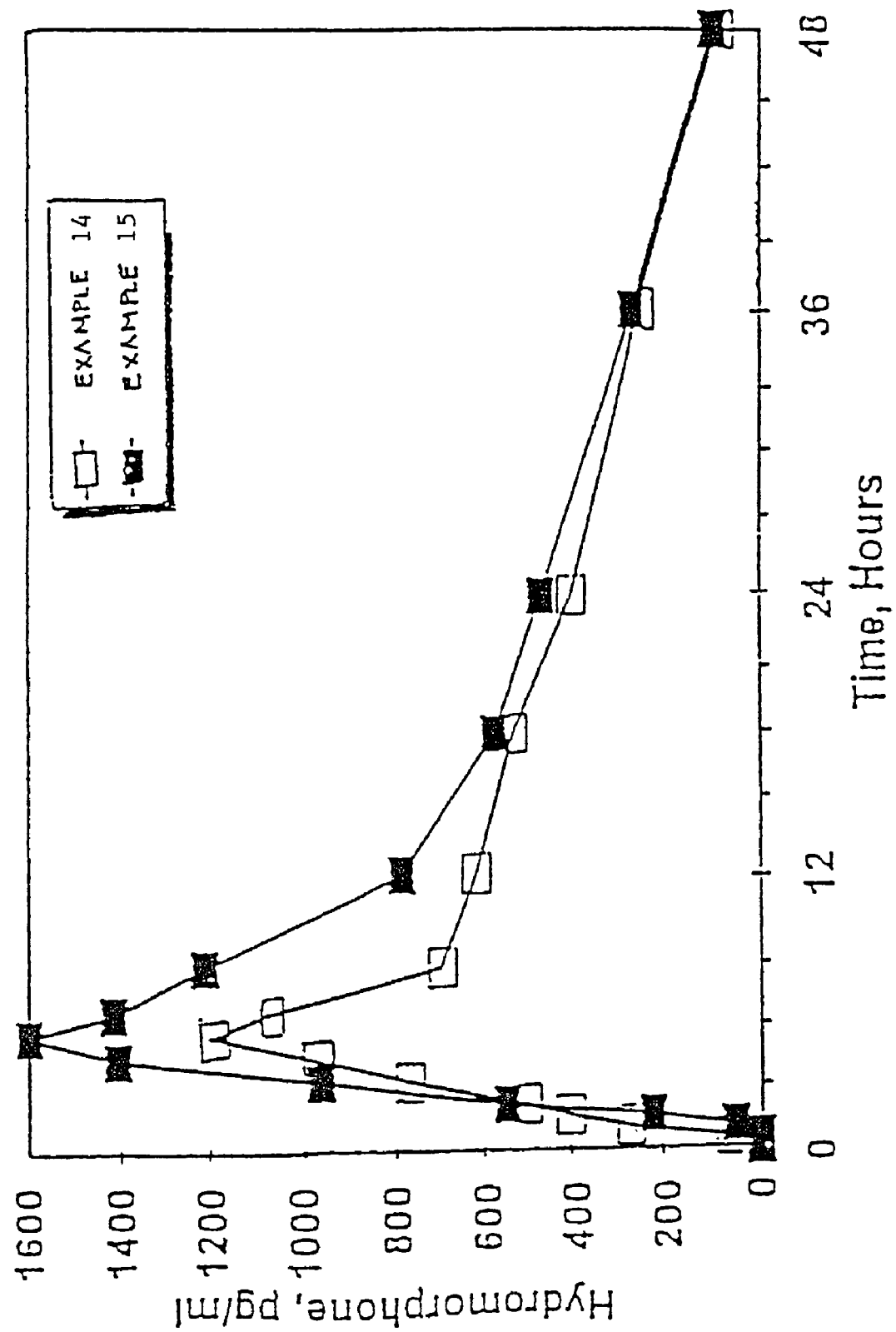

The plasma levels for Comparative Examples 14A and 15A are set forth in FIG. 4, whereas the plasma levels for Examples 14 and 15 are set forth in FIG. 5. The results for Examples 16–17 and Comparative Examples 16A and 17A are further set forth in Table 21, which provides data regarding area under the curve and percent absorbed as compared to immediate release (bioavailability), the peak plasma concentration ($C_{max}$), and the time to reach peak plasma concentration ($T_{max}$).

TABLE 19

| Group | AUC | % IR | $T_{max}$ | $C_{max}$ |
|---|---|---|---|---|
| Example 14 | 21059 | 101 | 4.9 | 1259 |
| Example 15 | 25833 | 106 | 4.6 | 1721 |
| Example 14A | 20903 | 100 | 0.85 | 3816 |
| Example 15A | 24460 | 100 | 1.15 | 3766 |

As can be ascertained from the results provided by Examples 14–15 and Comparative Examples 14A and 15A, there is a minimal food effect for both the immediate release tablets and the controlled-release beads of Examples 14 and 15, with a small increase in bioavailability for the controlled-release beads of Examples 14 and 15. The plasma levels again confirm that this product is suitable for once a day administration. In the 24th hour, the controlled-release product provides plasma levels of nearly 600 pg/ml and at the 12th hour provided plasma levels of over 700 pg/ml.

EXAMPLES 16–17

In Examples 16–17, a steady-state 3-way cross-over study is conducted for 4 days. In Comparative Example 16A, the subjects are dosed with 8 mg immediate release hydromorphone (2 Dilaudid 4 mg tablets) every 6 hours. In Example 16, 8 mg of the hydromorphone beads of Example 15 are administered every 12 hours. In Example 17, 8 mg of the hydromorphone beads of Example 13 are administered every 24 hours. Blood samples are taken on the fourth day.

The results for Examples 16–17 and Comparative Example 16A are further set forth in Table 20, which provides data regarding area under the curve and percent absorbed as compared to immediate release (bioavailability), the peak plasma concentration ($C_{max}$), and the time to reach peak plasma concentration ($T_{max}$).

TABLE 20

| Group | AUC | AUC* | $T_{max}$ | $C_{max}$ | $C_{max}$* |
|---|---|---|---|---|---|
| Example 16 | 62223 | 27595 | 5.5 | 3475 | 2232 |
| Example 17 | 39233 | 28879 | 4.8 | 2730 | 2189 |
| Comparative Example 16A | 47835 | 22236 | 1.0 | 3124 | 2163 |

*AUC = 0–12 hr. for Q12H, 0–24 hr. for Q24H, and 0–12 hr. for Q6H
*$C_{max}$ = $C_{max}$ minus zero time value With reference to the area under the curve (AUC) as a measure of bioavailability, it can be ascertained from the data provided in Table 20 that Comparative Example 16A and Examples 16 and 19 all have an equivalent AUC increased over the dosing interval, indicating that all dosage regimes are bioavailable.

Furthermore, in this study, Example 17, which was only dosed at 8 mg every 24 hours, shows that this formulation provides an excellent 24 hour preparation if the amount of beads are doubled to provide a once a day dosage of 16 mg, which is the equivalent amount of hydromorphone dosed by the immediate release formulation (4 mg every 6 hours). The minimum or trough concentration shown In FIG. 9 for Example 17 show that this product will be the equivalent of the 4 mg immediate release formulation (dosed every 6 hours), and therefore this would provide an excellent once a day product.

EXAMPLE 18

Controlled-Release Morphine Sulfate 30 Mg Formulation—Acrylic Polymer Coating

Example 18 is prepared in the same manner as the above Examples. The complete formula for the beads of Example 18 is set forth in Table 21 below:

TABLE 21

| Ingredients | Amt/Unit |
|---|---|
| Drug Loading | |
| Morphine Sulfate Powder | 30.0 mg |
| Lactose Hydrous Impalpable | 42.5 mg |
| Povidone | 2.5 mg |
| Nupareil PG 18/20 | 125.0 mg |
| Purified Water | qs |
| Opadry Red YS-1-1841 | 10.5 mg |
| Purified Water | qs |
| Retardant Coating | |
| Eudragit RS30D | 10.3 mg |
| Eudragit RL30D | 0.2 mg |
| Triethyl Citrate | 2.1 mg |
| Talc | 4.2 mg |
| Purified Water | qs |
| Second Overcoat | |
| Opadry Red YS-1-1841 | 12.0 |
| Purified Water | qs |
| Total | 239.3 mg |

The ratio of Eudragit® RS 30D to Eudragit® RL30D is 98:2. After completion of the final overcoat, the morphine beads are cured in a 45° C. oven for 2 days. The cured beads are then filled into gelatin capsules at a 30 mg strength.

The finished product is subjected to dissolution testing initially; after being stored for 3 months and 6 months at room temperature; and after exposure to accelerated storage conditions (40° C./75% RH) for one month, two months and three months. The results are set forth in Table 22 below:

TABLE 22

Dissolution (% Dissolved) Time (Hr)

| Storage Conditions | Testing Time | | | | |
|---|---|---|---|---|---|
| | 1 Hr. | 2 Hrs. | 4 Hrs. | 8 Hrs. | 12 Hrs. |
| Initial | 2.6 | 24.7 | 60.5 | 89.4 | 98.8 |
| 1 Month 40° C./75% RH | 5.8 | 27.3 | 62.0 | 89.8 | 99.1 |
| 3 Months 40° C./75% RH | 6.8 | 26.5 | 65.3 | 87.6 | 95.1 |
| 3 Months RT | 6.4 | 24.4 | 56.8 | 83.5 | 93.2 |
| 6 Months RT | 5.6 | 21.1 | 55.0 | 84.2 | 94.8 |

The dissolutions set forth in Table 22 show the beads of Example 18 to be stable.

A double-blind single dose cross-over study is then conducted in 12 subjects with regard to the dosage form of Example 18 against a standard, commercially available controlled-release morphine sulfate tablet (Comparative Example 18A; MS Contin® 30 mg tablets, available from the Purdue Frederick Company). The results are set forth in Table 23.

TABLE 23

| Pharmacokinetic Parameter | MS Contin (Fasted) | Example 18 5% Eudragit Coating (RS:RL, 98:2) (Fasted) |
|---|---|---|
| AUC | 76.2 | 93.6 |
| $T_{max}$ | 2.2 | 6.1 |
| $C_{max}$ | 9.4 | 6.2 |

From the data obtained from Example 18, it appears that the product may be suitable for once-a-day administration.

EXAMPLES 19–20

Therefore, in Examples 19–20, high load base beads are produced which have a higher load of morphine sulfate so that larger doses can be easily administered once-a-day. The high load beads are prepared via powder layering in a Glatt Rotor Processor. The formulation for Example 19–20 is set forth in Table 23 below:

TABLE 23

| Ingredients | High Load Bead mg |
|---|---|
| Morphine Sulfate | 30.0 |
| Lactose | 6.0 |
| Povidone C-30 | 1.25 |
| Sugar Beads | 7.75 |
| Opadry | 2.37 |
| Purified Water | qs |
| | 47.37 |

Since the base beads are different in comparison to the low load beads used in Example 18, more of the relatively soluble Eudragit® RL is included in the formula, as well as an extra HPMC protective coat between the Eudragit® layer and the morphine immediate release layer to further enhance stability.

The formula for the 60 mg dose is set forth in Table 24:

TABLE 24

| Ingredient | Amt/60 mg Unit (mg) |
|---|---|
| Morphine (high load) base beads | 85.26 |
| Retardant Coating | |
| Eudragit RS 30D | 4.2 |
| Eudragit RL 30D | 0.1 |
| Triethyl Citrate | 0.9 |
| Talc | 1.7 |
| Overcoatings | |
| Opadry Blue YS-1-10542A | 4.9 |
| Purified Water | qs |
| Morphine Sulfate Powder | 6.0 |
| Opadry Blue YS-1-10542A | 5.10 |
| Purified Water | qs |
| | 108.16 |

The beads are then cured in a 45° C. oven for 2 days, and thereafter are divided into two portions. Portion 1 is filled into hard gelatin capsules at a strength equivalent to 60 mg and portion 2 is filled into hard gelatin capsules at a strength equivalent to 30 mg.

Dissolution studies are conducted on both strength capsules. The data shows that the percent morphine dissolved is identical at both strengths. Stability studies are conducted with the 60 mg capsules. The results for the 60 mg capsules is set forth in Table 25 below:

TABLE 25

| Storage Conditions Time | Dissolution (% Dissolved) Time (Hr) | | | | | |
|---|---|---|---|---|---|---|
| | 1 Hr. | 2 Hrs. | 4 Hrs. | 8 Hrs. | 12 Hrs. | 14 Hrs. |
| Initial | 11.0 | 14.0 | 24.0 | 44.1 | 58.9 | 83.3 |
| 1 Month 40° C./75% RH | 11.9 | 14.9 | 25.0 | 43.6 | 56.6 | 85.1 |
| 2 Months 40° C./75% RH | 11.7 | 14.7 | 25.7 | 48.5 | 65.5 | 93.1 |

A bioavailability study is then conducted using the 30 mg strength capsule (Example 19=fasted; Example 20=fed) with MS Contin 30 mg—fasted (Example 19A) as a reference.

The results are set forth in Table 26.

TABLE 26

| Pharmacokinetic Parameter | MS Contin (Fasted) | Example 19 High Load with 10% IR Overcoat (Fasted) | Example 20 High Load with 10% IR Overcoat (Fed) |
|---|---|---|---|
| AUC | 114 | 141 | 118 |
| $T_{Max}$ | 2.8 | 12.9 | 8.0 |
| $C_{Max}$ | 11.6 | 4.0 | 5.4 |

From the data obtained, it appears that the product is suitable for once-a-day administration.

EXAMPLE 21

Controlled Release Acetaminophen (APAP) tablets are prepared in accordance with the present invention as follows:

First, immediate release APAP cores are prepared by compressing Compap coarse L into tablet cores weighing 555.6 mg. Compap coarse L contains approximately 90% APAP along with pharmaceutical grade excipients including a binder, disintegrant and lubricant, and is a directly compressible material commercially available from Mallinckrodt, Inc., St. Louis, Mo. The APAP tablet cores include approximately 500 mg of APAP. The Compap coarse L is compressed using a rotary tablet press equipped with a 7/16" round, standard concave cup, plain, tooling. The cores were compressed at a theoretical weight of 555.6 mg and at a hardness of about 8–9 Kp.

Next, the APAP tablet cores prepared above are coated with the controlled release coating of the present invention as follows:

Appropriate amounts of Eudragit RS-30D and Eudragit RL-30D are combined, and purified water-is added. The amount of purified water is calculated such that the final coating suspension will have a concentration of about 20% of solids polymer, plasticizer and talc. Then triethyl citrate is added with mixing for 15 minutes. Thereafter, talc is added with mixing for an additional 15 minutes. The appropriate quantity of APAP tablet cores are loaded into an Accela Cota coating pan. The coating suspension is sprayed from an appropriate spray gun until a weight gain of 4% per tablet of the polymer coating is attained.

After the spraying of the functional coat is completed, the tablets are sprayed with a film coat of Opadry. This coat is sprayed in a similar manner to the functional coat.

Further information concerning the Controlled Coated APAP tablets is set forth in Table 27 below:

TABLE 27

| Ingredients | mg/tab |
| --- | --- |
| APAP IR tablet cores | 555.60 |
| Eudragit RS-30D (solids) | 5.56 |
| Eudragit RL-30D (solids) | 16.66 |
| Triethyl citrate | 4.44 |
| Talc | 8.89 |
| Opadry White Y-5-7068 | 18.28 |
| Purified Water | qs |
| Total | 609.43 |

After completion of the coating process, the functional coated tablets are discharged into a curing tray and cured in a chamber at a temperature of 45° C. for 48 hours. The results of dissolution testing for the coated tablets are set forth in Table 28 below:

TABLE 28

| Test Period (Hours) | % APAP Dissolved |
| --- | --- |
| 1 | 2.1 |
| 2 | 4.8 |
| 4 | 10.4 |
| 8 | 20.0 |
| 12 | 29.2 |
| 18 | 41.2 |
| 24 | 52.1 |

EXAMPLE 22

In Example 22, controlled release Acetaminophen (APAP) tablets are prepared. To provide a faster dissolution is required, the amount of Eudragit RL-30D is increased and the amount of Eudragit RS-30D is decreased. Consequently, controlled release APAP tablets are prepared containing only Eudragit RL-30D and no Eudragit RS-30D. APAP cores are made as described in Example 4. Next, the APAP tablet cores prepared above are coated with the controlled release coating of the present invention as follows: Purified water is added to the Eudragit RL-30D. The amount of purified water is calculated such that the final coating suspension will have a concentration of about 20% of solids polymer, plasticizer and talc. Then, triethyl citrate is added with mixing for 15 minutes. Then, talc is added with mixing for an additional 15 minutes. The appropriate quantity of APAP tablet cores are loaded into an Accela Cota coating pan. The coating suspension is sprayed from an appropriate spray gun until a weight gain of 4% per tablet of the polymers is attained.

After the spraying of the functional coat is completed, the tablets are sprayed with a film coat of Opadry to prevent the tablets from sticking. This coat is sprayed in a similar manner to the functional coat.

Further information concerning the Controlled Release Coated APAP tablets is set forth in Table 29 below:

TABLE 29

| Ingredients | mg/tab |
| --- | --- |
| APAP IR tablet cores | 555.60 |
| Eudragit RL-30D (solids) | 22.22 |
| Triethyl citrate | 4.44 |
| Talc | 8.89 |
| Opadry White Y-5-7068 | 18.28 |
| Purified Water | qs |
| Total | 609.43 |

After completion of the coating process, the functional coated tablets are discharged into a curing tray and cured in a chamber at a temperature of 45° C. for 48 hours. Dissolution testing of the coated tablets provides the data set forth in Table 30 below:

TABLE 30

| Test Period (Hours) | % APAP Dissolved |
| --- | --- |
| 1 | 2.5 |
| 2 | 6.2 |
| 4 | 14.6 |
| 8 | 29.8 |
| 12 | 42.0 |
| 18 | 56.6 |
| 24 | 68.1 |

The examples provided above are not meant to be exclusive. Many other variations of the present invention would be obvious to those skilled in the art, and are contemplated to be within the scope of the appended claims.

What is claimed is:

1. A method for preparing a controlled release formulation comprising:
    preparing a solid substrate comprising a therapeutically active agent,
    overcoating said substrate with an aqueous dispersion of a plasticized water-insoluble acrylic polymer, and curing said coated substrate at a temperature greater than the glass transition temperature of the coating for at least 24 hours, until a curing endpoint is reached, at which endpoint said cured coated substrate when subjected to accelerated storage conditions of at least one month at 37° C./80% RH releases an amount of said therapeutically active agent upon in-vitro dissolution which does not vary at any given time point by more than 20% of the total amount of active agent released, when compared to the in-vitro dissolution of said cured coated substrate prior to being subjected to said accelerated storage conditions.

2. The method of claim 1, wherein said water-insoluble acrylic polymer is comprised of monomers selected from the group consisting of an ester of acrylic acid, an ester of methacrylic acid, an alkyl ester acrylic acid, an alkyl ester of methacrylic acid, and mixtures of any of the foregoing.

3. The method of claim 1, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

4. The method of claim 1, wherein said active agent is an opioid analgesic selected from the group consisting of hydromorphone, oxycodone, morphine, levorphanol, methadone, meperidine, heroin, dihydrocodeine, codeine, hydrocodone, tramadol, dihydromorphine, buprenorphone, mixed opiate receptor agonist-antagonists, salts, hydrates and solvents of any of the foregoing, and mixtures of any of the foregoing.

5. The method of claim 1, wherein said substrate is a tablet core.

6. The method of claim 1, wherein said formulation provides therapeutically effective blood levels of said systemically active therapeutic agent for about 24 hours.

7. The method of claim 1, wherein said step of comprises curing said coated substrate for a time period from about 24 to about 48 hours, until said endpoint is reached.

8. The method of claim 1, wherein said step of overcoating said substrate comprises including a portion of the amount of said active agent included in said formulation into a coating on said substrate.

9. The method of claim 1, wherein said water-insoluble acrylic polymer comprises a mixture of copolymers of acrylic and methacrylic esters having a molar ratio of ammonium groups to (meth)acrylic esters from about 1:20 to about 1:40.

10. The method of claim 1, wherein said step of overcoating said substrate comprises coating said substrate with said aqueous dispersion of water-insoluble acrylic polymer to a weight gain from about 2 to about 25 percent.

11. The method of claim 1, wherein said water-insoluble acrylic polymer comprises a mixture of a first copolymer of acrylic and methacrylic esters having a molar ratio of ammoniuni groups to (meth)acrylic esters of about 1:20 and a second copolymer of acrylic and methacrylic esters having a molar ratio of ammonium groups to (meth)acrylic esters of about 1:40, the ratio of said first copolymer to said second copolymer being from about 0:100 to about 100:0.

12. A method for preparing a controlled release formulation, comprising:

preparing a solid substrate comprising a therapeutically active agent, overcoating said substrate with an aqueous dispersion of a plasticized water-insoluble acrylic polymer, and curing said coated substrate at a temperature greater than the glass transition temperature of the coating for at least 24 hours, until a curing endpoint is reached, at which endpoint said cured coated substrate when subjected to accelerated storage conditions of at least one month at 37° C./80% RH and at least one month at 37° C./dry releases an amount of said therapeutically active agent upon in-vitro dissolution which does not vary at any given time point by more than 20% of the total amount of active agent released, when compared to the in-vitro dissolution of said cured coated substrate prior to being subjected to said accelerated storage conditions.

13. The method of claim 12, wherein said water-insoluble acrylic polymer is comprised of monomers selected from the group consisting of an ester of acrylic acid, an ester of methacrylic acid, an alkyl ester acrylic acid, an alkyl ester of methacrylic acid, and mixtures of any of the foregoing.

14. The method of claim 12, wherein said therapeutically active agent is selected from the group consisting of antihistamines, analgesics, non-steroidal anti-inflammatory agents, gastro-intestinals, anti-emetics, anti-epileptics, vasodilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

15. The method of claim 12, wherein said active agent is an opioid analgesic selected from the group consisting of hydromorphone, oxycodone, morphine, levorphanol, methadone, meperidine, heroin, dihydrocodeine, codeine, hydrocodone, tramadol, dihydromorphine, buprenorphone, mixed opiate receptor agonist-antagonists, salts, hydrates and solvents of any of the foregoing, and mixtures of any of the foregoing.

16. The method of claim 12, wherein said substrate is a tablet core.

17. The method of claim 12, wherein said formulation provides therapeutically effective blood levels of said systemically active therapeutic agent for about 24 hours.

18. The method of claim 12, wherein said step of curing comprises curing said coated substrate for a time period from about 24 to about 48 hours, until said endpoint is reached.

19. The method of claim 12, wherein said step of overcoating said substrate comprises including a portion of the amount of said active agent included in said formulation is incorporated into a coating on said substrate.

20. The method of claim 12, wherein said water-insoluble acrylic polymer comprises a mixture of copolymers of acrylic and methacrylic esters having a molar ratio of ammonium groups to (meth)acrylic esters from about 1:20 to about 1:40.

21. The method of claim 12, wherein said step of overcoating said substrate comprises coating said substrate with said aqueous dispersion of water-insoluble acrylic polymer to a weight gain from about 2 to about 25 percent.

22. The method of claim 12, wherein said water-insoluble acrylic polymer comprises a mixture of a first copolymer of acrylic and methacrylic esters having a molar ratio of ammonium groups to (meth)acrylic esters of about 1:20 and a second copolymer of acrylic and methacrylic esters having a molar ratio of ammonium groups to (meth)acrylic esters of about 1:40, the ratio of said first copolymer to said second copolymer being from about 0:100 to about 100:0.

23. A method for preparing a controlled release formulation, comprising:
preparing a solid substrate comprising a therapeutically active agent,
overcoating said substrate with an aqueous dispersion of a plasticized water-insoluble acrylic polymer, and
curing said coated substrate at a temperature greater than the glass transition temperature of the coating for at least 24 hours, until a curing endpoint is reached, at which endpoint said cured coated substrate when subjected to storage conditions of at least one month at 37° C./80% RH and at least one month at room temperature releases an amount of said therapeutically active agent upon in-vitro dissolution which does not vary at any given time point by more than 20% of the total amount of active agent released, when compared to the in-vitro dissolution of said cured coated substrate prior to being subjected to said accelerated storage conditions.

24. The method of claim 23, wherein said water-insoluble acrylic polymer is comprised of monomers selected from the group consisting of an ester of acrylic acid, an ester of methacrylic acid, an alkyl ester acrylic acid, an alkyl ester of methacrylic acid, and mixtures of any of the foregoing.

25. The method of claim 23, wherein said therapeutically active agent is selected from the group consisting of anti-histamines, analgesics, non-steroidal anti-inflammatory agents, gastro-intestinals, anti-emetics, anti-epileptics, vaso-dilators, anti-tussive agents, expectorants, anti-asthmatics, hormones, diuretics, anti-hypotensives, anti-hypertensives, bronchodilators, antibiotics, antivirals, antihemorrhoidals, steroids, hypnotics, psychotropics, antidiarrheals, mucolytics, sedatives, decongestants, laxatives, vitamins, and stimulants.

26. The method of claim 23, wherein said active agent is an opioid analgesic selected from the group consisting of hydromorphone, oxycodone, morphine, levorphanol, methadone, meperidine, heroin, dihydrocodeine, codeine, hydrocodone, traniadol, dihydromorphine, buprenorphone, mixed opiate receptor agonist-antagonists, salts, hydrates and solvents of any of the foregoing, and mixtures of any of the foregoing.

27. The method of claim 23, wherein said substrate is a tablet core.

28. The method of claim 23, wherein said formulation provides therapeutically effective blood levels of said systemically active therapeutic agent for about 24 hours.

29. The method of claim 23, wherein said step of curing comprises curing said coated substrate for a time period from about 24 to about 48 hours, until said endpoint is reached.

30. The method of claim 23, wherein said step of overcoating said substrate comprises including a portion of the amount of said active agent included in said formulation is incorporated into a coating on said substrate.

31. The method of claim 23, wherein said water-insoluble acrylic polymer comprises a mixture of copolymers of acrylic and methacrylic esters having a molar ratio of ammonium groups to (meth)acrylic esters from about 1:20 to about 1:40.

32. The method of claim 23, wherein said step of overcoating said substrate comprises coating said substrate with said aqueous dispersion of water-insoluble acrylic polymer to a weight gain from about 2 to about 25 percent.

33. The method of claim 23, wherein said water-insoluble acrylic polymer comprises a mixture of a first copolymer of acrylic and methacrylic esters having a molar ratio of ammonium groups to (meth)acrylic esters of about 1:20 and a second copolymer of acrylic and methacrylic esters having a molar ratio of ammonium groups to (meth)acrylic esters of about 1:40, the ratio of said first copolymer to said second copolymer being from about 0:100 to about 100:0.

34. The method of claim 1, wherein said plasticized water-insoluble acrylic polymer has a permeability that is unaffected by pH conditions prevailing in the gastrointestinal tract and is present in said overcoating in an amount sufficient to obtain a controlled release of said therapeutically active agent, after curing of the coated substrate, when measured by the USP Paddle or Basket Method at 100 rpm at 900 ml aqueous buffer (pH between 1.6 and 7.2) at 37° C. of from about 0% to about 42.5% (by wt.) active agent released after 1 hour, from about 5% to about 60% (by wt.) active agent release after 2 hours, from about 15% to about 75% (by wt.) active agent release after 4 hours, and from about 20% to about 90% % (by wt.) active agent released after 8 hours.

35. The method of claim 1, wherein said cured coated substrate, after being subjected to said accelerated conditions, releases an amount of said therapeutically active agent upon in-vitro dissolution which does not vary at any given time point by more than about 15% of the total amount of active agent released, when compared to the in-vitro dissolution of said cured coated substrate prior to being subjected to said accelerated conditions.

36. The method of claim 12, wherein said plasticized water-insoluble acrylic polymer has a permeability that is unaffected by pH conditions prevailing in the gastrointestinal tract and is present in said overcoating in an amount sufficient to obtain a controlled release of said therapeutically active agent, after curing of the coated substrate, when measured by the USP Paddle or Basket Method at 100 rpm at 900 ml aqueous buffer (pH between 1.6 and 7.2) at 37° C. of from about 0% to about 42.5% (by wt.) active agent released after 1 hour, from about 5% to about 60% (by wt.) active agent release after 2 hours, from about 15% to about 75% (by wt.) active agent release after 4 hours, and from about 20% to about 90% % (by wt.) active agent released after 8 hours.

37. The method of claim 12, wherein said cured coated substrate, after being subjected to said accelerated conditions, releases an amount of said therapeutically active agent upon in-vitro dissolution which does not vary at any given time point by more than about 15% of the total amount of active agent released, when compared to the in-vitro dissolution of said cured coated substrate prior to being subjected to said accelerated conditions.

38. The method of claim 23, wherein said plasticized water-insoluble acrylic polymer has a permeability that is unaffected by pH conditions prevailing in the gastrointestinal tract and is present in said overcoating in an amount sufficient to obtain a controlled release of said therapeutically active agent, after curing of the coated substrate, when measured by the USP Paddle or Basket Method at 100 rpm at 900 ml aqueous buffer (pH between 1.6 and 7.2) at 37° C. of from about 0% to about 42.5% (by wt.) active agent released after 1 hour, from about 5% to about 60% (by wt.) active agent release after 2 hours, from about 15% to about 75% (by wt.) active agent release after 4 hours, and from about 20% to about 90% (by wt.) active agent released after 8 hours.

39. The method of claim 23, wherein said cured coated substrate, after being subjected to said accelerated conditions, releases an amount of said therapeutically active agent upon in-vitro dissolution which does not vary at any given time point by more than about 15% of the total amount of active agent released, when compared to the in-vitro dissolution of said cured coated substrate prior to being subjected to said accelerated conditions.

* * * * *